(12) United States Patent
Tokunaga

(10) Patent No.: US 10,062,955 B2
(45) Date of Patent: Aug. 28, 2018

(54) SAMPLE ANALYZER AND REAGENT INFORMATION OBTAINING METHOD

(75) Inventor: Kazutoshi Tokunaga, Kakogawa (JP)

(73) Assignee: SYSMEX CORPORATION, Kobe-shi (JP)

( * ) Notice: Subject to any disclaimer, the term of this patent is extended or adjusted under 35 U.S.C. 154(b) by 0 days.

(21) Appl. No.: 13/071,022

(22) Filed: Mar. 24, 2011

(65) Prior Publication Data

US 2011/0232372 A1    Sep. 29, 2011

(30) Foreign Application Priority Data

Mar. 25, 2010 (JP) .................. 2010-069186

(51) Int. Cl.
*G01N 35/02* (2006.01)
*G01N 35/04* (2006.01)
(Continued)

(52) U.S. Cl.
CPC ..... *H01Q 1/2216* (2013.01); *G01N 35/00732* (2013.01); *B01L 3/545* (2013.01);
(Continued)

(58) Field of Classification Search
None
See application file for complete search history.

(56) References Cited

U.S. PATENT DOCUMENTS 5,500,651 A * 3/1996 Schuermann ............... 342/42
5,827,479 A * 10/1998 Yamazaki ............ G01N 35/04
                                                           422/561

(Continued)

FOREIGN PATENT DOCUMENTS

JP    02-065529    6/1990
JP    05-143799    11/1993
(Continued)

OTHER PUBLICATIONS

Eom et al., "An Efficient Reader Anticollision Algorithm in Dense RFID Networks With Mobile RFID Readers", IEEE Transactions on Industrial Electronics, vol. 56, No. 7, Jul. 2009, pp. 2326-2336.

*Primary Examiner* — Kathryn Wright
(74) *Attorney, Agent, or Firm* — Metrolexis Law Group, PLLC

(57) ABSTRACT

A sample analyzer and a method for obtaining reagent information are disclosed, wherein the sample analyzer analyzes a sample by using a reagent contained in a reagent container, comprising a first reagent container holder configured to hold a first reagent container containing a first reagent, a first electronic tag, on which a reagent information regarding the first reagent is recorded, attached to the first reagent container; a second reagent container holder configured to hold a second reagent container containing a second reagent, a second electronic tag, on which a reagent information regarding the second reagent is recorded, attached to the second reagent container; an antenna that is arranged between the first reagent container holder and the second reagent container holder, and is configured to receive a radio wave from each of the first and second electronic tags; and a reagent information obtainer unit configured to obtain the reagent information recorded on the first electronic tag based on a radio wave received from the first electronic tag, and to obtain the reagent information recorded on the second electronic tag based on a radio wave received from the second electronic tag.

14 Claims, 14 Drawing Sheets

(51) Int. Cl.
*H01Q 1/22* (2006.01)
*G01N 35/00* (2006.01)
*B01L 3/00* (2006.01)

(52) U.S. Cl.
CPC ........... *G01N 2035/00673* (2013.01); *G01N 2035/00782* (2013.01); *G01N 2035/00821* (2013.01); *G01N 2035/0443* (2013.01)

(56) References Cited

U.S. PATENT DOCUMENTS

| | | | |
|---|---|---|---|
| 5,885,529 A | 3/1999 | Babson et al. | |
| 2002/0190126 A1* | 12/2002 | Benhammou et al. | 235/451 |
| 2004/0207564 A1 | 10/2004 | Kawakami et al. | |
| 2004/0258565 A1* | 12/2004 | Watari | 422/64 |
| 2005/0069861 A1* | 3/2005 | Zimmermann et al. | 435/1.1 |
| 2009/0134978 A1* | 5/2009 | Imai | 340/10.6 |
| 2010/0073141 A1* | 3/2010 | Nishida et al. | 340/10.3 |
| 2011/0095864 A1* | 4/2011 | Trueeb et al. | 340/10.1 |
| 2011/0223062 A1* | 9/2011 | Minemura et al. | 422/67 |

FOREIGN PATENT DOCUMENTS

| | | | |
|---|---|---|---|
| JP | 2005283344 A | * | 10/2005 |
| JP | 2008-203007 | * | 9/2008 |
| JP | 2008-306495 | | 12/2008 |
| JP | 2009-210444 A | | 9/2009 |
| WO | 2009-130775 | | 10/2009 |
| WO | WO 2010058736 | * | 5/2010 |

* cited by examiner

SAMPLE ANALYZER AND REAGENT INFORMATION OBTAINING METHOD

FIELD OF THE INVENTION

The present invention relates to a sample analyzer, in particular, to a sample analyzer mounting a reagent container including an electronic tag on which reagent information is recorded.

BACKGROUND

A sample analyzer mounting a reagent container including an electronic tag on which reagent information is recorded is conventionally known.

Japanese Patent Publication No. 2009/210444 discloses an automatic analyzer including: a reagent container holder of circular ring shape for holding a plurality of reagent containers including a wireless IC tag, on which reagent information is recorded, in two columns of an inner circumferential column and an outer circumferential column; an inner circumferential side antenna for emitting a radio wave to the wireless IC tag of the reagent container held in the reagent container holder of the inner circumferential column; an outer circumferential side antenna for emitting a radio wave to the wireless IC tag of the reagent container held in the reagent container holder of the outer circumferential column; and an information reading/recording unit for receiving the radio wave returned from the wireless IC tag from the inner circumferential side antenna and the outer circumferential side antenna. In the automatic analyzer, the inner circumferential side antenna is arranged on the inner side of the reagent container holder of the inner circumferential column, and the outer circumferential side antenna is arranged on the outer side of the reagent container holder of the outer circumferential column.

However, in the automatic analyzer described in Japanese Patent Publication No. 2009/210444, antennas need to be arranged at the inner side of the reagent container holder of the inner circumferential column and the outer side of the reagent container holder of the outer circumferential column. Thus, there is a problem that the number of components increases. Furthermore, there is also a problem that the device main body enlarges since the region on the inner side of the reagent container holder of the inner circumferential column and the region on the outer side of the reagent container holder of the outer circumferential column need to be ensured to arrange the antennas.

SUMMARY

The scope of the present invention is defined solely by the appended claims, and is not affected to any degree by the statements within this summary.

A first aspect of the present invention is a sample analyzer that analyzes a sample by using a reagent contained in a reagent container, comprising: a first reagent container holder configured to hold a first reagent container containing a first reagent, wherein a first electronic tag, on which a reagent information regarding the first reagent is recorded, is attached to the first reagent container; a second reagent container holder configured to hold a second reagent container containing a second reagent, wherein a second electronic tag, on which a reagent information regarding the second reagent is recorded, is attached to the second reagent container; an antenna that is arranged between the first reagent container holder and the second reagent container holder, and is configured to receive a radio wave from each of the first and second electronic tags; and a reagent information obtainer unit configured to obtain the reagent information recorded on the first electronic tag based on a radio wave received from the first electronic tag, and to obtain the reagent information recorded on the second electronic tag based on a radio wave received from the second electronic tag.

A second aspect of the present invention is a method for obtaining reagent information of a reagent in a reagent container, comprising: arranging an antenna between a first reagent container holder configured to hold a first reagent container and a second reagent container holder configured to hold a second reagent container, wherein a first electronic tag on which a reagent information is recorded is attached to the first reagent container and a second electronic tag on which a reagent information is recorded is attached to the second reagent container; moving the first reagent container holder so that the first electronic tag faces the antenna when the first electronic tag is a target of reading a reagent information; moving the second reagent container holder so that the second electronic tag faces the antenna when the second electronic tag is a target of reading a reagent information; receiving a radio wave, by the antenna, from an electronic tag facing the antenna; and obtaining a reagent information based on the radio wave received by the antenna.

DETAILED DESCRIPTION OF THE EMBODIMENT

The embodiments embodying the present invention will be described based on the drawings.

The configuration of an immune sample analyzer 1 according to a first embodiment of the present invention will be now described with reference to FIGS. 1 to 15.

A sample analyzer 1 according to a first embodiment of the present invention is an apparatus for carrying out examinations on various items, such as a protein related to an infectious disease (e.g., hepatitis B, hepatitis C, etc.), a tumor marker, and a thyroid hormone using samples such as blood.

The sample analyzer 1 is an apparatus for quantitatively measuring or qualitatively measuring, e.g., antigens, antibodies and the like contained in a sample (blood specimen) such as blood, which is the measurement target. When quantitatively measuring the antigen contained in the sample, the sample analyzer 1 is configured to bond magnetic particles (R2 reagent) to a capture antibody (R1 reagent) bonded to an antigen contained in the sample, and thereafter, attracting the bound antigen, capture antibody, and the magnetic particles to a magnet (not shown) of a primary BF (Bound Free) separator 11 to remove the R1 reagent containing non-reactive (free) capture antibody. The sample analyzer 1 then bonds the antigen bound with the magnetic particles and the labeled antibody (R3 reagent), and thereafter, attracts the bound magnetic particles, the antigen, and the labeled antibody to a magnet (not shown) of a secondary BF separator 12 to remove the R3 reagent containing non-reactive (free) labeled antibody. The dispersion liquid (R4 reagent) and the light emitting substrate (R5 reagent) that emits light in the reaction process with the labeled antibody are added, and a light emitting amount generated through the reaction of the labeled antibody and the light emitting substrate is measured. The antigen contained in the sample that bonds with the labeled antibody is quantitatively measured through such processes.

Figure 1:
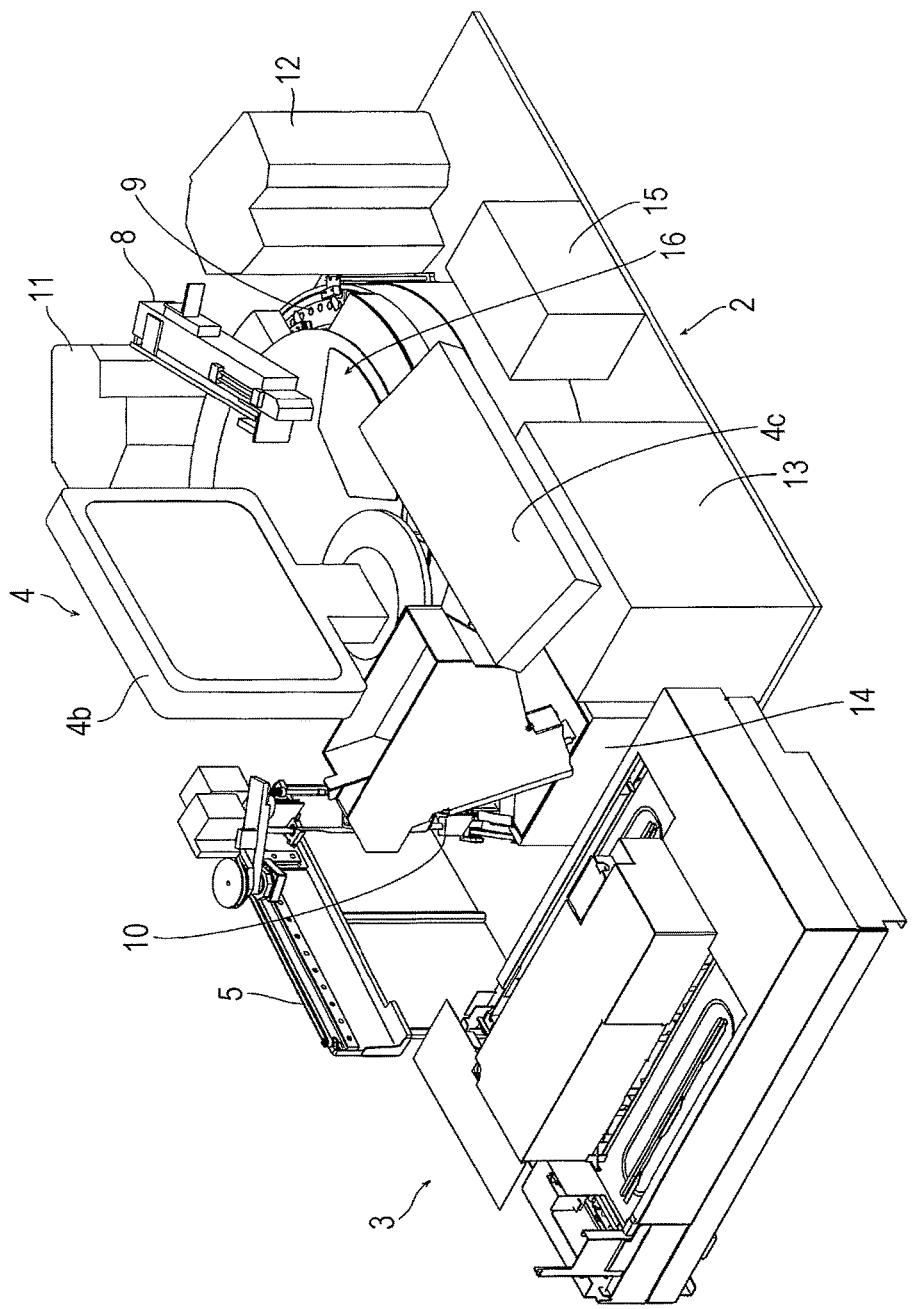
FIG. 1 is a perspective view showing an overall configuration of a sample analyzer according to one embodiment of the present invention.
Figure 2:
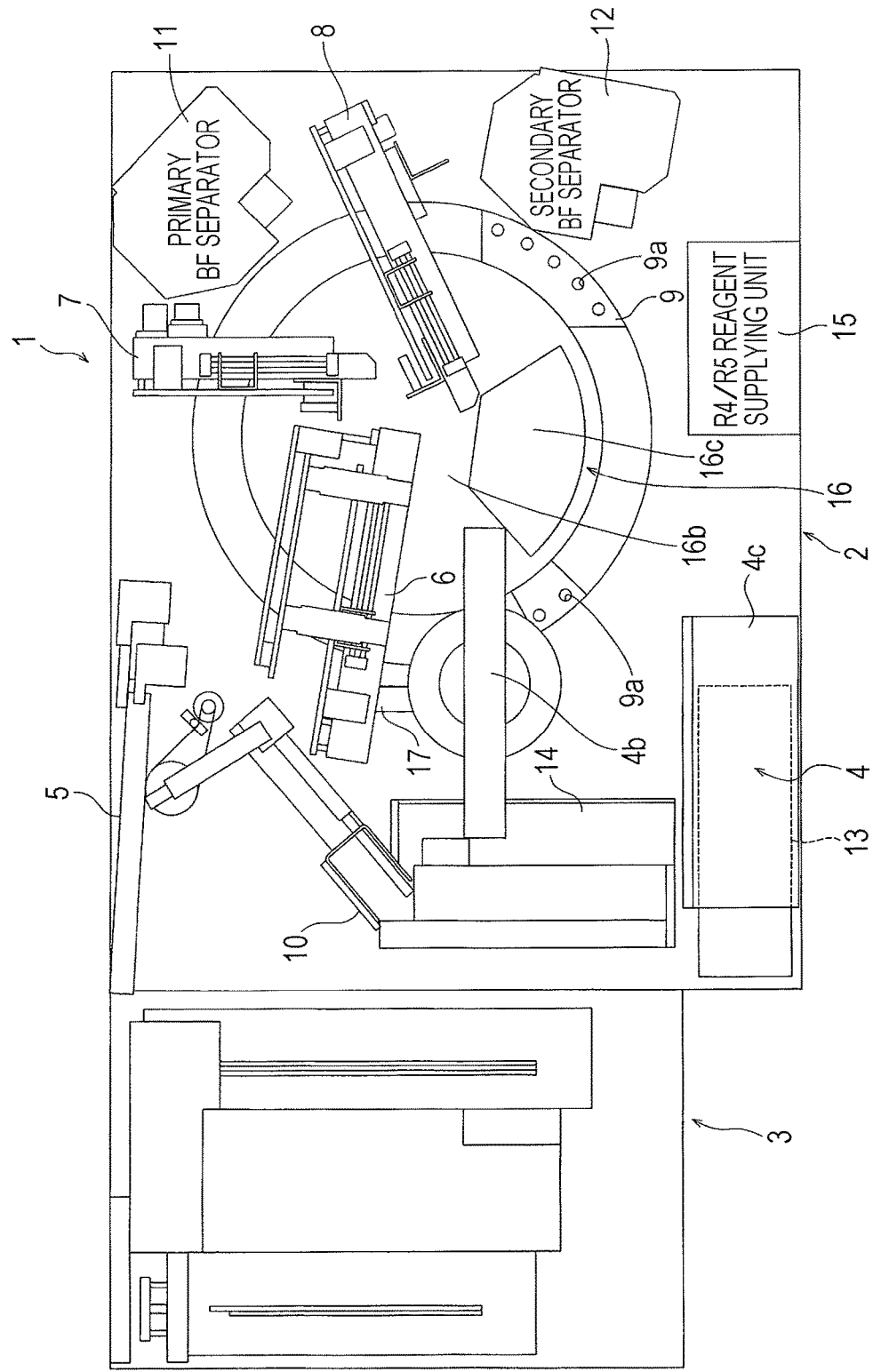
FIG. 2 is a plan view showing the overall configuration of the sample analyzer according to one embodiment shown in FIG. 1.

As shown in FIGS. 1 and 2, the sample analyzer 1 includes a measurement mechanism section 2, a sample transport section (sampler) 3 arranged adjacent to the measurement mechanism section 2, and a control device 4 including a PC (personal computer) electrically connected to the measurement mechanism section 2.

The sample transport section 3 is configured to transport a rack mounted with a plurality of test tubes (not shown) containing the samples. The sample transport section 3 is configured to transport the test tube containing the sample up to a sample aspirating position by means of a sample dispensing arm 5.

Figure 3:
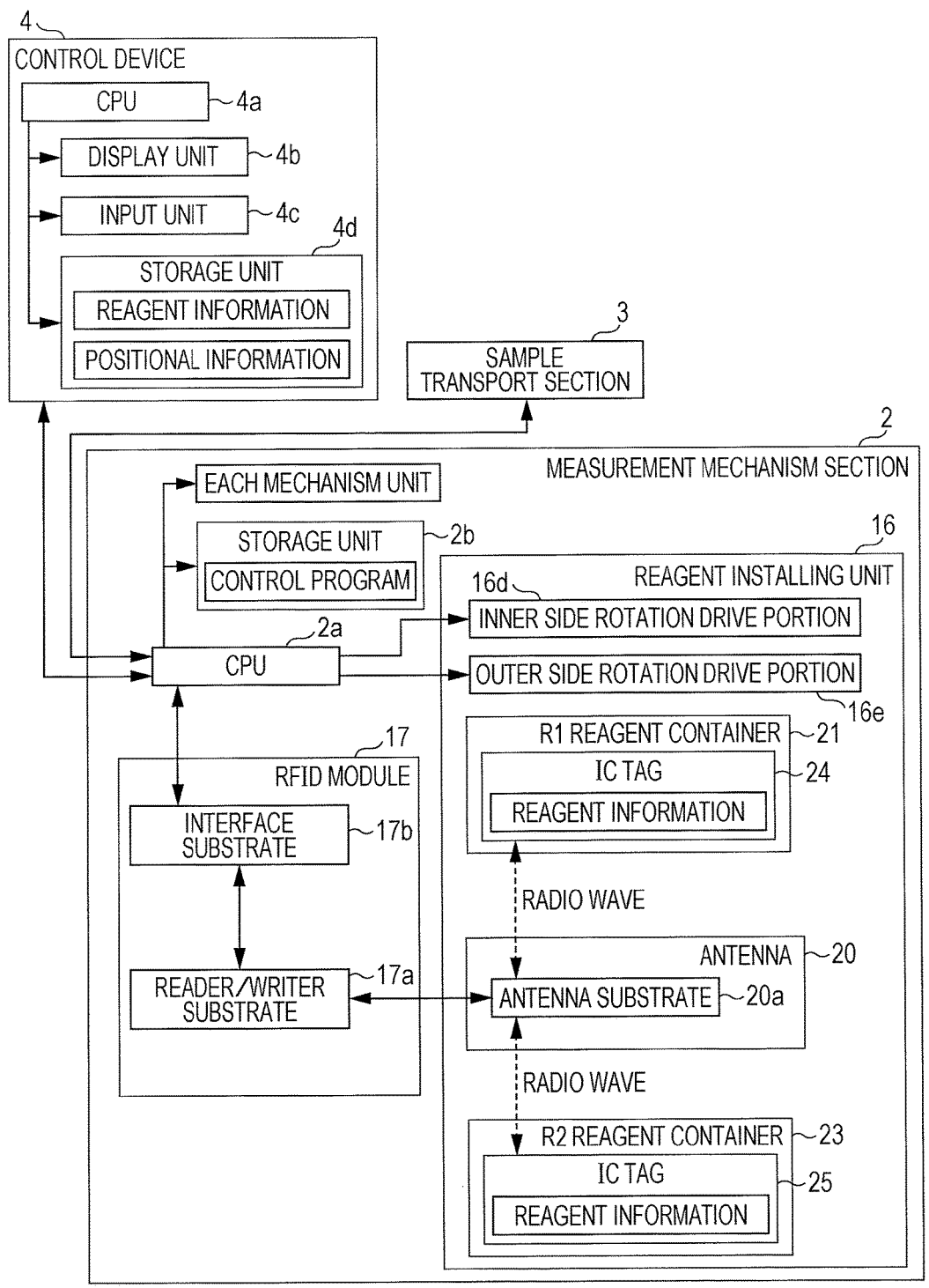
FIG. 3 is a block diagram for describing the configuration of the sample analyzer according to one embodiment shown in FIG. 1.

As shown in FIG. 3, the control device 4 includes a CPU 4a, a display unit 4b, an input unit 4c, and a storage unit 4d. The CPU 4a causes the measurement mechanism section 2 (hereinafter described as CPU 2a) to carry out the measurement based on the measurement condition and the like input by the user using the input unit 4c, and analyzing the measurement result obtained by the measurement mechanism 2 and displaying the analysis result on the display unit 4b. The storage unit 4d includes a hard disc, and individually stores the reagent information and the positional information of a R1 reagent container 21, a R3 reagent container 22, and a R2 reagent container 23, to be described later. The storage unit 4d is described in detail.

As shown in FIG. 2, the measurement mechanism section 2 is configured by a sample dispensing arm 5, an R1 reagent dispensing arm 6, a R2 reagent dispensing arm 7, a R3 reagent dispensing arm 8, a reaction unit 9, a cuvette supplying unit 10, the primary BF separator 11, the secondary BF separator 12, a pipette tip supplying unit 13, a detection unit 14, a R4/R5 reagent supplying unit 15, a reagent installing unit 16, and an RFID (Radio Frequency IDentification) module 17.

As shown in FIG. 3, each mechanism (various dispensing arms, reaction unit 9, and the like) in the measurement mechanism section 2 is controlled by the CPU 2a arranged in the measurement mechanism section 2. The sample transport section 3 is also configured to be controlled by the CPU 2a. Furthermore, the measurement mechanism section 2 includes the storage unit 2b, where a control program for causing the CPU 2a to execute the operation control of each mechanism of the measurement mechanism section 2 is stored in the storage unit 2b.

As shown in FIG. 2, the cuvette supplying unit 10 is configured to accommodate a plurality of cuvettes (not shown), and sequentially supplies cuvettes to the sample aspirating position one by one by means of the sample dispensing arm 5.

The R1 reagent dispensing arm 6 is configured to aspirate the R1 reagent installed at the reagent installing unit 16, and dispense (discharge) the aspirated R1 reagent into the cuvette mounted at the sample discharging position. The R1 reagent dispensing arm 6 transfers the cuvette mounted at the sample discharging position to the reaction unit 9 with a catcher (not shown).

The pipette tip supplying unit 13 transports a plurality of inserted pipette tips (not shown) to the tip attachment position one by one by means of the sample dispensing arm 5. The pipette tip is attached to the distal end of the pipette of the sample dispensing arm 5.

The sample dispensing arm 5 attaches the pipette tip at the tip attachment position, and then aspirating the sample in the test tube transported to the sample aspirating position by the sample transport section 3, and dispensing (discharging) the sample to the cuvette at the sample discharging position dispensed with the R1 reagent by the R1 reagent dispensing arm 6.

The R2 reagent dispensing arm 7 aspirates the R2 reagent installed at the reagent installing unit 16. The R2 reagent dispensing arm 7 is configured to dispense (discharge) the aspirated R2 reagent into the cuvette containing the R1 reagent and the sample.

The reaction unit 9 is formed to a substantially circular ring shape so as to surround the periphery of the reagent installing unit 16 having a substantially circular shape in plan view. The reaction unit 9 is configured to rotate in a clockwise direction, and moves the cuvette held in the cuvette holding portion 9a to each processing position where various processes (dispensing of reagent, and the like) are performed.

The primary BF separator 11 is configured to separate (B/F separation) the non-reacting R1 reagent (unnecessary component) and the magnetic particles from the specimen in the cuvette after transferring the cuvette containing the sample, the R1 reagent, and the R2 reagent from the reaction unit 9 to the primary BF separator 11 with a catcher (not shown).

The R3 reagent dispensing arm 8 has a function of aspirating the R3 reagent installed at the reagent installing unit 16. The R3 reagent dispensing arm 8 is configured to dispense (discharge) the aspirated R3 reagent into the cuvette when the cuvette accommodating the specimen after the B/F separation by the primary BF separator 11 is transferred from the primary BF separator 11 to the reaction unit 9.

The secondary BF separator 12 is configured to separate the non-reacting R3 reagent (unnecessary component) and the magnetic particles from the specimen in the cuvette after transferring the cuvette containing the specimen after the B/F separation by the primary BF separator 11 and the R3 reagent from the reaction unit 9 to the secondary BF separator 12 with a catcher (not shown).

The R4/R5 reagent supplying unit 15 is configured to dispense the R4 reagent and the R5 reagent, in order, to the cuvette containing the specimen after the B/F separation by the secondary BF separator 12 with a tube (not shown).

The detector 14 is arranged to measure the amount of antigen contained in a sample by obtaining the light generated in the reaction process of the labeled antibody bound to the antigen of the sample performed with a predetermined process and the light emitting substrate with a photo multiplier tube.

As shown in FIG. 2, the reagent installing unit 16 includes a housing 16a (see FIG. 4) having a substantially cylindrical shape, a lid 16b arranged to cover the housing 16a from the upper side, and an open/close portion 16c which is arranged at the lid 16b and which is opened and closed when the user changes the R1 reagent container 21, the R3 reagent container 22, and the R2 reagent container 23, to be described later. An openable/closable window (not shown) is formed at the upper surface of the lid 16b corresponding to the position where the R1 reagent, the R2 reagent, and the R3 reagent are aspirated. The R1 reagent, the R2 reagent, and the R3 reagent are aspirated by the R1 reagent dispensing arm 6, the R2 reagent dispensing arm 7, and the R3 reagent dispensing arm 8, respectively, through the window.

Figure 4:
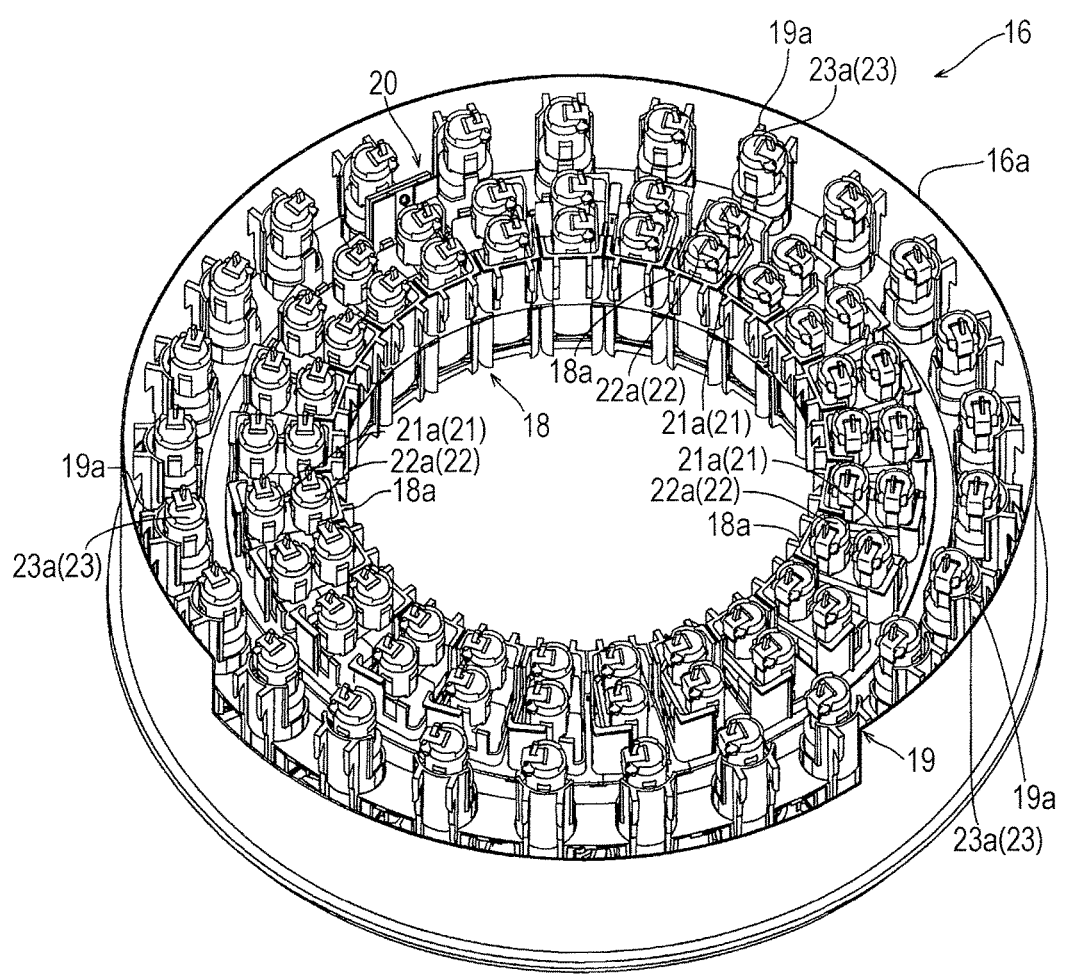
FIG. 4 is a perspective view showing the interior of the reagent installing unit of the sample analyzer according to one embodiment shown in FIG. 1.
Figure 5:
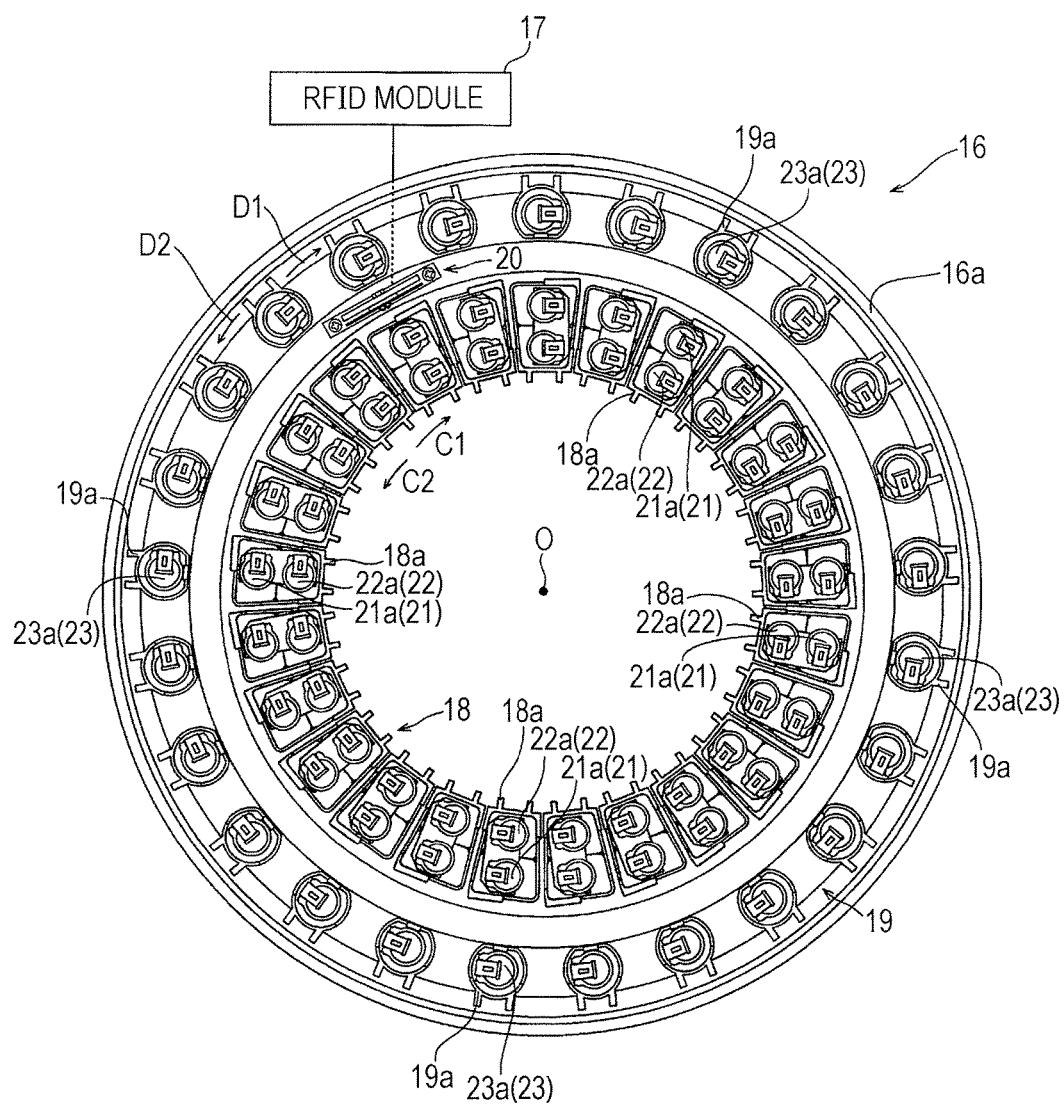
FIG. 5 is a plan view showing the interior of the reagent installing unit of the sample analyzer according to one embodiment shown in FIG. 1.
Figure 6:
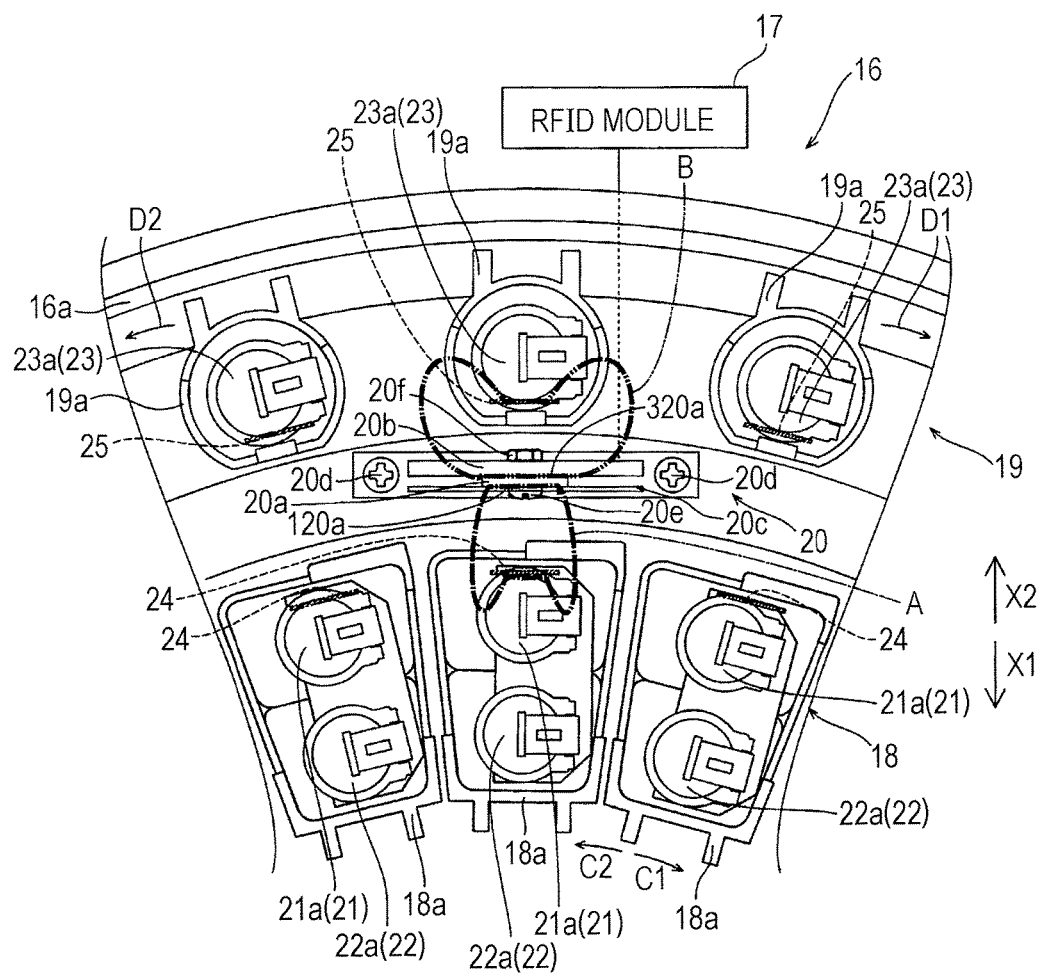
FIG. 6 is an enlarged plan view showing a state of reading an IC tag of a reagent container of the reagent installing unit according to one embodiment shown in FIG. 1.

In a first embodiment, the R1/R3 installing portion 18, an R2 installing portion 19, and one antenna 20 are arranged inside the housing 16a of the dispensing installing unit 16, as shown in FIG. 4 and FIG. 5. Specifically, as shown in FIG. 4 to FIG. 6, the R1/R3 installing portion 18 and the R2 installing portion 19 are formed to a substantially circular ring shape with the center O substantially the same as the center O of the housing 16a when seen in plan view. The R1/R3 installing portion 18 is arranged on the inner peripheral side (center O side in FIG. 5) of the R2 installing portion 19, and the antenna 20 is arranged on the outer peripheral side (opposite side of center O) of the R1/R3 installing portion 18 and on the inner peripheral side of the R2 installing portion 19. In other words, the antenna 20 is arranged so as to be sandwiched by the R1/R3 installing portion 18 and the R2 installing portion 19 in plan view.

Figure 7:
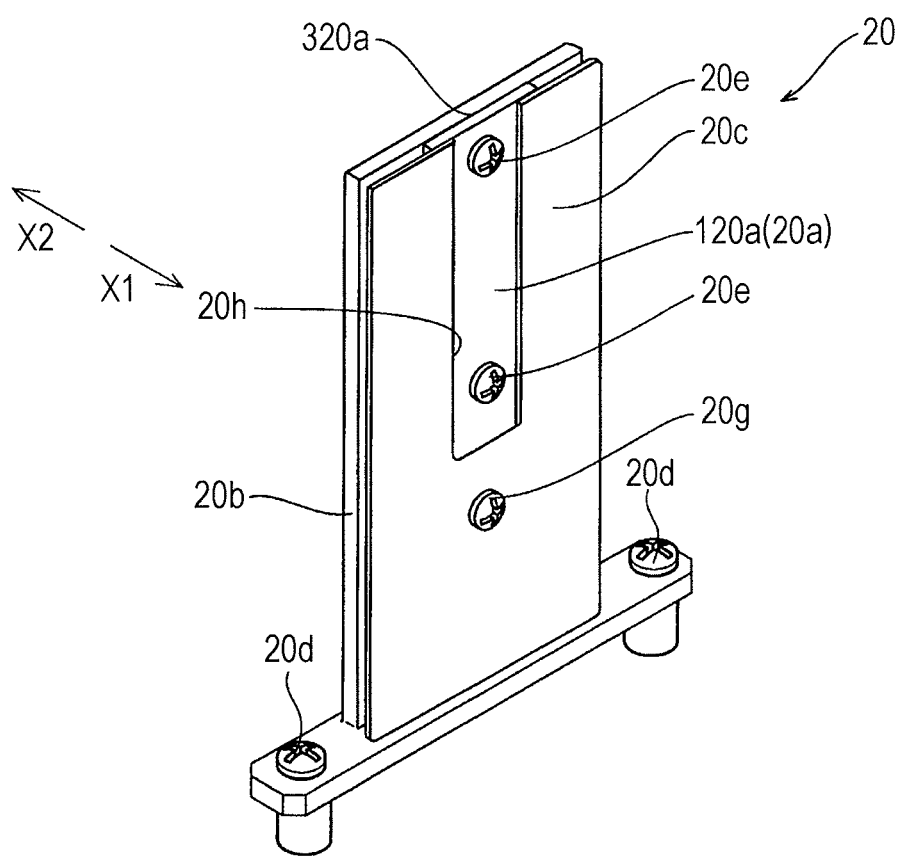
FIG. 7 is a perspective view showing an antenna of the reagent installing unit according to one embodiment shown in FIG. 1.
Figure 8:
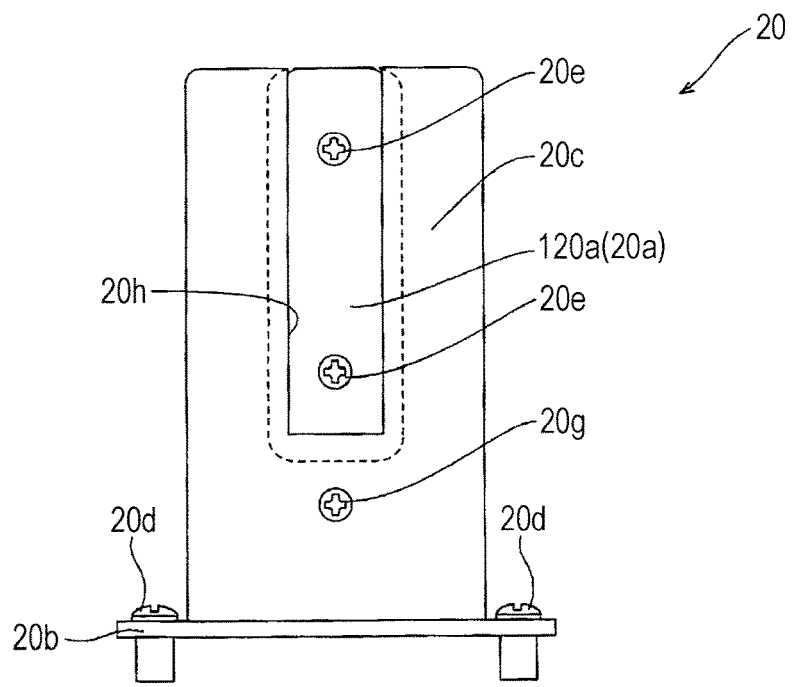
FIG. 8 is a front view showing the antenna of the reagent installing unit according to one embodiment shown in FIG. 1.

As shown in FIG. 7 and FIG. 8, the antenna 20 includes an antenna substrate 20a, a substrate attachment portion 20b for fixing the antenna substrate 20a from the outer side (direction of arrow X2, see FIG. 6), and a metal plate 20c, arranged on the inner side of the antenna 20 (direction of arrow X1, see FIG. 6), to be attached to the substrate attachment portion 20b so as to sandwich the antenna substrate 20a with the substrate attachment portion 20b. As shown in FIG. 6, the lower part of the substrate attachment portion 20b is fixed to the bottom surface of the housing 16a with a screw 20d. In other words, the antenna 20 is fixed to the housing 16a.

Figure 9:
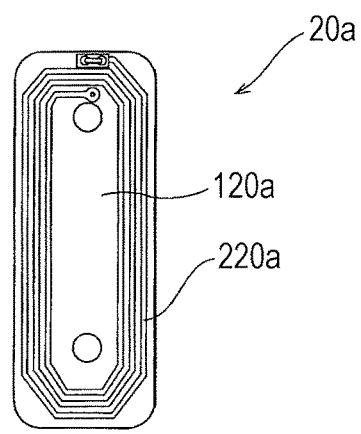
FIG. 9 is a plan view showing an antenna substrate of the antenna according to one embodiment shown in FIG. 1.

As shown in FIG. 9, the antenna substrate 20a is configured by forming a coil-like antenna wiring 220a on the surface 120a (see FIG. 7) on the direction of the arrow X1 of the flat plate shaped substrate. The radio wave can be transmitted and received through the coil-like antenna wiring 220a. As shown in FIG. 6, the antenna substrate 20a is arranged inside the substrate attachment portion 20b so that the surface 120a on the side of the direction of the arrow X1 of the antenna substrate 20a faces the center O (see FIG. 5) of the housing 16a.

In the first embodiment, the antenna substrate 20a is configured to emit the read radio wave and the write radio wave from the surface 120a on the side of the direction of the arrow X1 towards the inner side (center O side of FIG. 5 (side of the direction of the arrow X1)) of the reagent installing unit 16, and is configured to emit the read radio wave and the write radio wave from the surface 320a on the side of the direction of the arrow X2 towards the outer side (R2 installing portion 19 side (side of the direction of the arrow X2)). The antenna substrate 20a is configured to be able to receive the response radio wave emitted from the IC tags 24 and 25 in response to the read radio wave. The antenna 20 is configured to be able to perform read and write with respect to the IC tag 24 of the R1 reagent container 21 arranged on the side in the direction of the arrow X1, and is configured to be able to perform read and write with respect to the IC tag 25 of the R2 reagent container 23 arranged on the side in the direction of the arrow X2. The antenna substrate 20a is connected to a reader/writer substrate 17a, described below, of the RFID module 17.

The substrate attachment portion 20b is made of resin capable of transmitting radio wave. Thus, the read radio wave and the write radio wave emitted from the surface 320a on the side in the direction of the arrow X2 of the antenna substrate 20a towards the outer side (side in the direction of the arrow X2) transmit through the substrate attachment portion 20b and reach the R2 installing portion 19, and the response radio wave emitted from the IC tag 25 transmits through the substrate attachment portion 20b and reach the antenna substrate 20a. As shown in FIG. 7, the antenna substrate 20a is fixed to the substrate attachment portion 20b with a screw 20e and a nut 20f (see FIG. 6).

The metal plate 20c is made of aluminum plate material capable of absorbing radio waves (read radio wave, write radio wave, and response radio wave). The metal plate 20c is fixed to the substrate attachment portion 20b with a screw 20g and a nut (not shown) so as to be arranged on the side in the direction of the arrow X1 of the antenna 20 while sandwiching the antenna substrate 20a with the substrate attachment portion 20b.

The metal plate 20c includes a substantially U-shaped cutout 20h. The antenna substrate 20a is configured to emit radio wave towards the inner side (side in the direction of arrow X1) of the reagent installing unit 16 through the cutout 20h, where the radio wave of the antenna substrate 20a that does not pass through the cutout 20h is absorbed by the metal plate 20c. In other words, the metal plate 20c limits the reading range and the writing range on the side in the direction of the arrow X1 of the antenna 20 (antenna substrate 20a) by limiting the range A (thick chain dashed line shown in FIG. 6) of the read radio wave and the write radio wave emitted from the antenna substrate 20a towards the side in the direction of the arrow X2 and the range of the response radio wave the antenna substrate 20a receives from the side in the direction of the arrow X1.

The metal plate is not arranged on the side in the direction of the arrow X2 of the antenna 20. Thus, the range (range B shown in FIG. 6 (thick double dashed line)) of the read radio wave and the write radio wave emitted from the antenna substrate 20a towards the side in the direction of the arrow X2 and the range of the response radio wave the antenna substrate 20a receives from the side in the direction of the arrow X2 are not limited. As a result, the range B (thick double dashed line) of the read radio wave and the write radio wave emitted from the antenna substrate 20a towards the side in the direction of the arrow X2 is configured to become greater than the range A (thick chain dashed line) of the read radio wave and the write radio wave emitted from the antenna substrate 20a towards the side in the direction of the arrow X1.

The reagent installing unit 16 includes an inner side rotation drive portion 16c (see FIG. 3) for rotating the R1/R3 installing portion 18 in the direction of an arrow C1 and in the direction of an arrow C2 with the center O as the center of rotation, and an outer side rotation drive portion 16d (see FIG. 3) for rotating the R2 installing portion 19 in the direction of the arrow D1 and the direction of the arrow D2 with the center O as the center of rotation. The inner side rotation drive portion 16c and the outer side rotation drive portion 16d are configured so that the drive is individually controlled by the CPU 2a.

As shown in FIG. 5, the R1/R3 installing portion 18 includes twenty-five R1/R3 holding members 18a, which are made of resin capable of transmitting the radio wave, arranged at an equal angle (about 14.4 degrees). Each R1/R3 holding member 18a holds the R1 reagent container 21 for accommodating the R1 reagent containing the capture antibody, and the R3 reagent container 22 for accommodating the R3 reagent containing the labeled body. The R1/R3 holding member 18a is configured such that the R1 reagent container 21 is held on the outer side (R2 installing portion 19 side) and the R3 reagent container 22 is held on the inner side (center O side).

The R2 installing portion 19 includes twenty-five R2 holding members 19a, which are made of resin capable of transmitting the radio wave, arranged at an equal angle (about 14.4 degrees). Each R2 holding member 19a holds the R2 reagent container 23 for accommodating the R2 reagent containing the magnetic particles.

The R1/R3 installing portion 18 is arranged on the inner peripheral side of the R2 installing portion 19, and the R1 reagent containers 21 and the R2 reagent containers 23 are arranged in the same number (twenty-five), and thus the interval between the R1 reagent containers 21 is smaller than the interval between the R2 reagent containers 23. In other words, the R1 reagent containers 21 are arranged closer to each other than the R2 reagent containers 23. The R1 reagent containers 21, the R3 reagent containers 22, and the R2 reagent containers 23 are configured to be installed and changed by the user.

Figure 10:
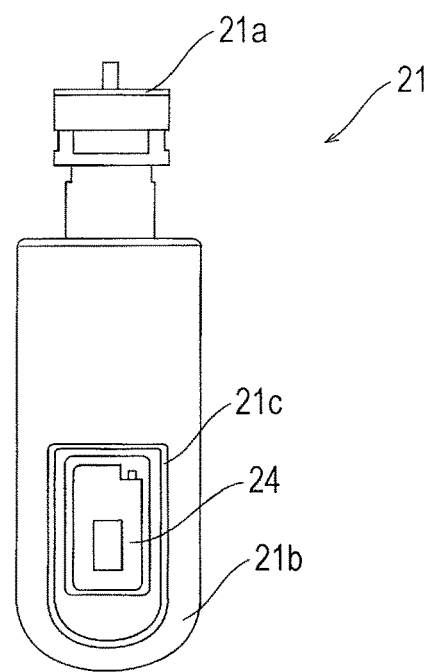
FIG. 10 is a side view showing an R1 reagent container of the reagent installing unit according to one embodiment shown in FIG. 1.
Figure 11:
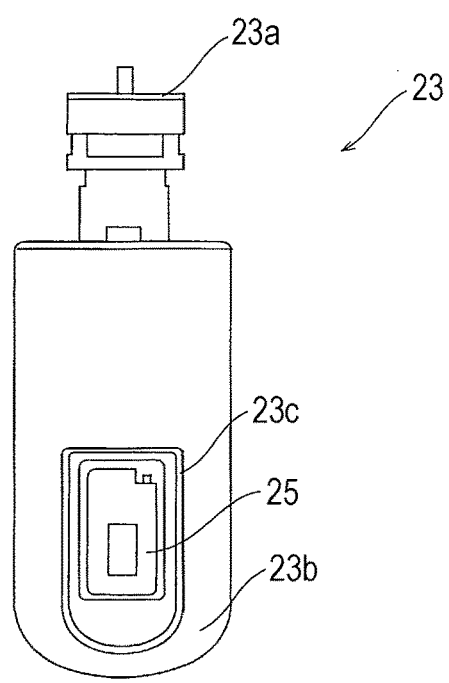
FIG. 11 is a side view showing an R2 reagent container of the reagent installing unit according to one embodiment shown in FIG. 1.

As shown in FIG. 10, the R1 reagent container 21 is formed with a lid 21a that opens and closes when aspirating the R1 reagent, and a reagent accommodating portion 21b for accommodating the R1 reagent. As shown in FIG. 11, the R2 reagent container 23 is formed with a lid 23a that opens and closes when aspirating the R2 reagent, and a reagent accommodating portion 23b for accommodating the R2 reagent. As shown in FIG. 6, the R3 reagent container 22 and the R1 reagent container 21 have substantially a similar shape, and the R3 reagent container 22 is formed with a lid 22a that opens and closes when aspirating the R3 reagent, and a reagent accommodating portion (not shown) for accommodating the R3 reagent. The lids 21a and 22a are configured to open and close with the rotation of the R1/R3 installing portion 18, and the lid 23a is configured to open and close with the rotation of the R2 installing portion 19.

In the first embodiment, as shown in FIG. 10, an IC tag attachment portion 21c, to where the IC tag 24 is to be attached, is formed on the side surface arranged on the outer side (direction of arrow X2 in FIG. 6) of the reagent accommodating portion 21b of the R1 reagent container 21. In other words, the IC tag 24 of the R1 reagent container 21 is attached to the side surface in the direction of the arrow X2 of the reagent accommodating portion 21b so as to face the outer side (direction of the arrow X2) of the reagent installing unit 16 and to face the front surface position of the surface 120a in the direction of the arrow X1 of the antenna substrate 20a when arranged in the R1/R3 installing portion 18, as shown in FIG. 6.

As shown in FIG. 11, an IC tag attachment portion 23c, where the IC tag 25 is to be attached, is formed on the side surface arranged on the inner side (direction of arrow X1 in FIG. 6) of the reagent accommodating portion 23b of the R2 reagent container 23. In other words, the IC tag 25 of the R2 reagent container 23 is attached to the side surface in the direction of the arrow X1 of the reagent accommodating portion 23b so as to face the inner side (direction of the arrow X1) of the reagent installing unit 16 and to face the front surface position of the surface 320a in the direction of the arrow X2 of the antenna substrate 20a when arranged in the R2 installing portion 19, as shown in FIG. 6. An IC tag is not attached to the side surface of the R3 reagent container 22, as opposed to the R1 reagent container 21.

The IC tag 24 records the reagent information of the R1 reagent of the R1 reagent container 21, and the reagent information of the R3 reagent of the R3 reagent container 22 held in the R1/R3 holding member 18a common with the R1 reagent container 21. The IC tag 25 records the reagent information of the R2 reagent of the R2 reagent container 23.

Figure 12:
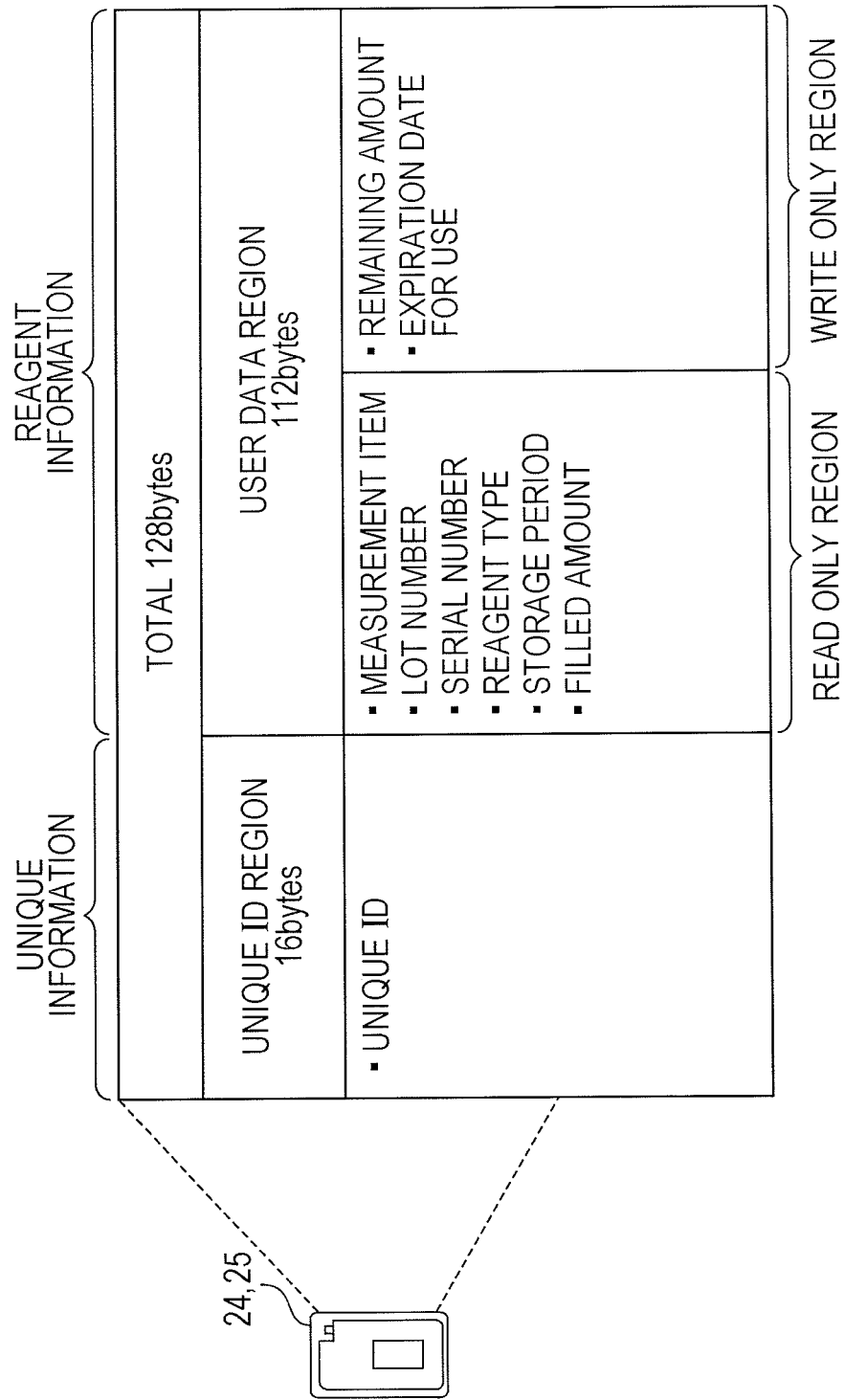
FIG. 12 is a conceptual diagram showing the unique information and the reagent information stored in the IC tag according to one embodiment shown in FIG. 1.

As shown in FIG. 12, the IC tags 24 and 25 are configured to be able to store 128 bytes of information. Among the storage capacity of 128 bytes, 16 bytes are assigned for the unique ID region indicating the unique information, and 112 bytes are assigned for the user data region indicating the reagent information. The unique ID region is the region where the unique ID for individually identifying the IC tags 24 and 25 is recorded, and only read can be carried out. The user data region is the region where the user can freely write information. The user data region is set with a region (read only region) where only read is carried out and write is not carried out, and a region (writeable region) where both read and write are carried out.

The unique ID is used when the CPU 2a encrypts the reagent information. Thus, the reagent information cannot be decrypted if the unique ID is different even if the reagent information is duplicated to a different IC tag, and hence the reagent information and the reagent of the reagent container are suppressed from being wrongly communicated.

The measurement item, the lot number, the serial number, the reagent type (type specifying information), the storage period, and the filled amount regarding the reagent container (R1 reagent container 21 or R2 reagent container 23) given the IC tag (IC tag 24 or 25) are recorded in the read only region, and the remaining amount and the expiration date for use are written in the writable region. The IC tag 24 also records the information regarding the R3 reagent container 22. The information is not written to the writable region of the IC tag 24 attached to the R1 reagent container 21 installed in the R1/R3 installing portion 18 for the first time, and the IC 25 attached to the R2 reagent container 23 installed in the R2 installing portion 19 for the first time.

The measurement item shows the measurement item performed with the reagent accommodated in the reagent container attached with the IC tag. The reagent type shows whether the reagent container attached with the IC tag is the R1 reagent container 21 or the R2 reagent container 23. The storage period shows the period the reagent can be stored. The filled amount shows the number of measurements that can be carried out with the reagent. The remaining amount shows the number of measurements that can be carried out with the reagent. The expiration date for use shows the date until the reagent can be used. The expiration date for use is set when the relevant reagent starts to be used.

In the first embodiment, the IC tags 24 and 25 are configured so that read and write are carried out at the front surface position (facing position) of the antenna 20, as shown in FIG. 6. In other words, the IC tag 24 of the R1 reagent container 21 is configured to be arranged at the position facing the surface 120a on the side in the direction of the arrow X1 of the antenna 20, and the IC tag 25 of the R2 reagent container 23 is configured to be arranged at the position facing the surface 320a on the side in the direction of the arrow X2 of the antenna 20.

The IC tags 24 and 25 are configured to emit the response radio wave containing the reagent information recorded in the IC tags 24 and 25 based on the read radio wave emitted from the antenna 20. The IC tags 24 and 25 are configured to rewrite the reagent information recorded in the IC tag to the new reagent information contained in the write radio wave based on the write radio wave emitted from the antenna 20. The reagent information is recorded in the IC tags 24 and 25 in the encrypted state.

As shown in FIG. 6, the IC tag 24 is configured so that read and write are carried out by the read radio wave and the write radio wave in the range A (thick chain dashed line) emitted from the antenna 20. The IC tag 25 is configured so that read and write are carried out by the read radio wave and the write radio wave in the range B (thick double dashed line) emitted from the antenna 20. The interval between the adjacent R1/R3 holding members 18a and the range A are set so that read and write are not carried out on the other IC tags 24 when read and write are carried out on a specific IC tag 24. The interval between the adjacent R2 holding members 19a and the range B are set so that read and write are not carried out on the other IC tags 25 when read and write are carried out on a specific IC tag 25.

As shown in FIG. 3, the respective reagent information of the twenty-five R1 reagent containers 21, the twenty-five R2 reagent containers 23, and the twenty-five R3 reagent containers 22 are individually stored in the storage unit 4d of the control device 4 apart from the IC tags 24 and 25. The storage unit 4d stores the respective initial position of the twenty-five R1 reagent containers 21, the twenty-five R3 reagent containers 22, and the twenty-five R2 reagent containers 23, and the rotation angle from the respective initial position of the R1/R3 installing portion 18 and the R2 installing portion 19 as positional information. The storage unit 4d thus stores the positional information and the reagent information of twenty-five R1 reagent containers 21, the twenty-five R3 reagent containers 22, and the twenty-five R2 reagent containers 23 in a corresponded state. The reagent information is stored in the storage unit 4d of the control device 4 in the decrypted state.

When the power supply (not shown) of the sample analyzer 1 is turned ON, the IC tags (IC tags 24 and 25) of all the reagent containers installed in the reagent installing unit 16 are read, and the positional information and the reagent information of each reagent container are obtained. If the reagent information is stored in the storage unit 4d, the CPU 4a of the control device 4 updates the reagent information stored in the storage unit 4d to the reagent information obtained from the IC tag when the power supply is turned ON. Thus, even if the R1 reagent container 21, the R3 reagent container 22, and the R2 reagent container 23 are changed to a new R1 reagent container 21, R3 reagent container 22, and R2 reagent container 23, respectively, while the power supply of the sample analyzer 1 is turned OFF, the reagent information stored in the storage unit 4d of the control device 4 can be updated to the information of the reagent currently installed at the reagent installing unit 16.

As shown in FIG. 2, the RFID module 17 is arranged exterior to the reagent installing unit 16, and includes a reader/writer substrate 17a, and an interface substrate 17b for intermediating the reader/writer substrate 17a and the CPU 2a, as shown in FIG. 3.

The reader/writer substrate 17a is configured to emit the read radio wave and the write radio wave having a frequency band of about 13.56 MHz from the antenna 20 based on an instruction from the CPU 2a. Furthermore, the reader/writer substrate 17a is configured to obtain the reagent information from the response radio wave emitted from the IC tags 24 and 25 in response to the read radio wave and received by the antenna 20, and to output the reagent information to the CPU 2a.

The measurement operation of the sample analyzer 1 (measurement mechanism section 2) according to a first embodiment of the present invention is now described with reference to FIG. 3 and FIG. 13.

First, when the power supply of the measurement mechanism section 2 is turned ON, the CPU 2a of the measurement mechanism section 2 initializes the program in step S1 and executes an initialization process such as operation check of each unit of the measurement mechanism section 2.

Thereafter, the reagent information reading process is performed in step S2. The reagent information reading process is described in detail below.

In step S3, whether a measurement instruction by the user is made is determined by the CPU 2a. The measurement instruction by the user is transmitted to the CPU 2a through the control device 4 (see FIG. 3). If it is determined that the measurement instruction by the user is not made, the process proceeds to step S6.

If it is determined that the measurement instruction by the user is made in step S3, the reagent aspirating/reagent information writing process is carried out by the CPU 2a in step S4. The reagent aspirating/reagent information writing process is described in detail below.

Subsequently, the sample is measured in step S5. In step S6, whether the instruction to shut down by the user is made is determined by the CPU 2a. The process returns to step S3 if it is determined that the instruction of shutdown is not made. If it is determined that the instruction of shutdown is made, the shutdown of the measurement mechanism section 2 is carried out by the CPU 2a in step S7. The measurement operation of the CPU 2a of the measurement mechanism section 2 is terminated in such a manner.

Figure 13:
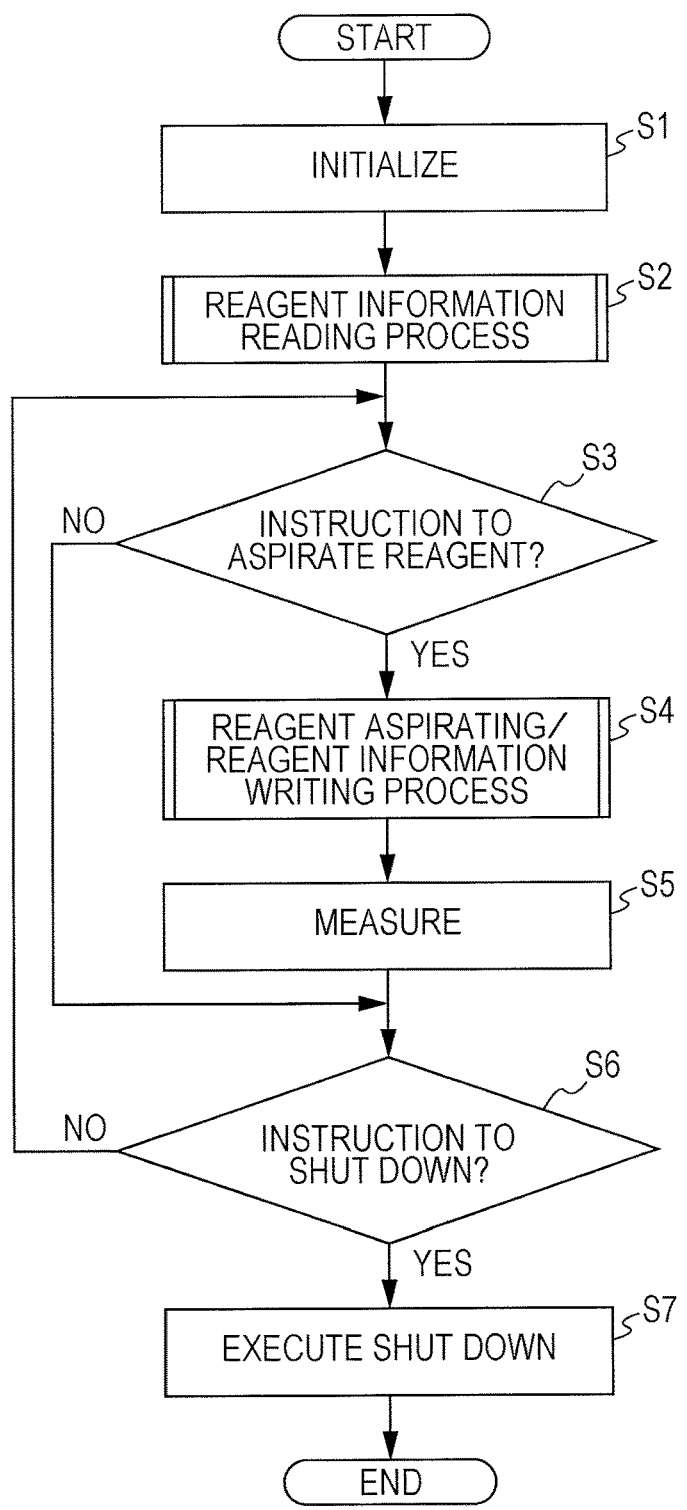
FIG. 13 is a flowchart showing the measurement operation of the sample analyzer F according to one embodiment shown in FIG. 1.
Figure 14:
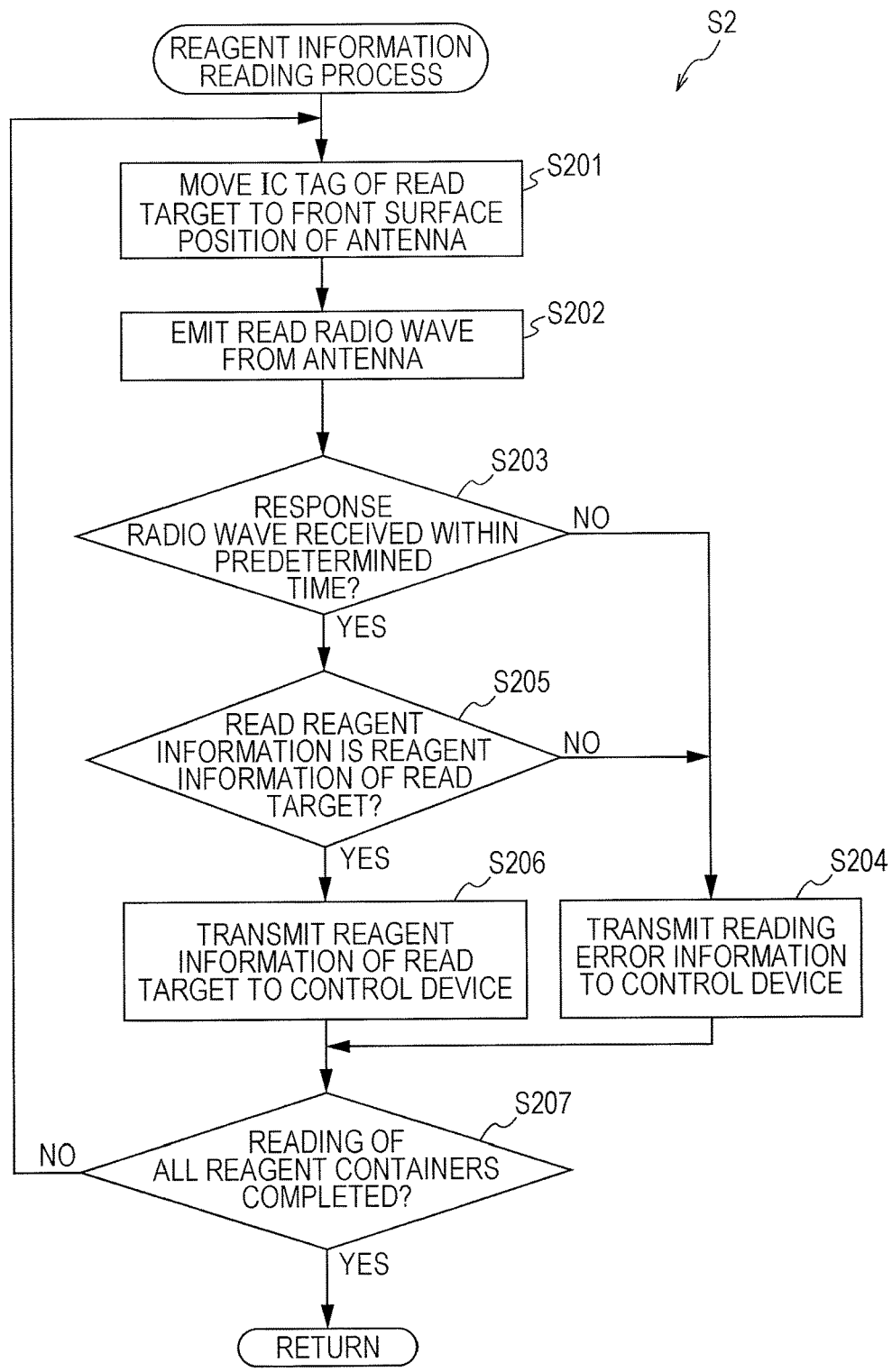
FIG. 14 is a flowchart showing a reagent information reading process of the sample analyzer according to one embodiment shown in FIG. 1.

With reference to FIG. 6 and FIG. 14, the reagent information reading process of the sample analyzer 1 according to the first embodiment of the present invention shown in step S2 of FIG. 13 is described below in detail.

First, in step S201, the R1/R3 installing portion 18 (R2 installing portion 19) is rotated in the direction of the arrow C1 (D1) or the arrow C2 (D2) (see FIG. 6) so that the IC tag 24 (IC tag 25) of the read target is positioned at the position (front surface position) facing the surface 120a on the side in the direction of the arrow X1 (surface 320a on the side in the direction of the arrow X2) of the antenna 20 by the CPU 2a. In step S202, the antenna 20 emits the read radio wave to the IC tag 24 (IC tag 25) of the read target by the control of the CPU 2a and the reader/writer substrate 17a. In this case, the IC tag 25 (IC tag 24) that is not the read target may receive the read radio wave emitted from the antenna 20 and emit the response radio wave.

In step S203, whether the response radio wave emitted from the IC tag 24 (IC tag 25) in correspondence with the read radio wave is received by the antenna 20 within a predetermined time is determined by the CPU 2a. In other words, whether the reagent information obtained by the reader/writer substrate 17a of the RFID module 17 based on the response radio wave received from the antenna 20 is output to the CPU 2a within a predetermined time is determined by the CPU 2a. If it is determined that the antenna 20 did not receive the response radio wave within a predetermined time, determination is made that the reading failed, and the reading error information is transmitted to the control device 4 by the CPU 2a in step S204. A notification that reading of the reagent information of the reagent container positioned at the predetermined position (reagent information of the reagent container of read target) failed is displayed on the display unit 4b of the control device 4. The process then proceeds to step S207.

If it is determined that the antenna 20 received the response radio wave within the predetermined time in step S203, whether the reagent information contained in the response radio wave received by the antenna 20 is the reagent information of the read target is determined by the CPU 2a in step S205. In this case, the CPU 2a determines whether the reagent information of the read target based on the reagent type (type specifying information) obtained from the response radio wave. If it is determined that the reagent information contained in the response radio wave is not the reagent information of the read target, the process proceeds to step S204. The reagent information from the IC tag 25 (IC tag 24) that is not the read target is thus suppressed from being mistakenly used as the reagent information of the read target.

If it is determined that the reagent information contained in the response radio wave is the reagent information of the read target, the reagent information of the read target contained in the response radio wave is transmitted from the CPU 2a to the control device 4 in step S206. When the antenna 20 receives a plurality of response radio waves, and the reagent information of the read target exists in the plurality of response radio waves, only the reagent information of the read target is transmitted to the control device 4. In the control device 4, the reagent information of the storage unit 4d is updated based on the reagent information received from the CPU 2a. The process then proceeds to step S207.

Finally, in step S207, whether the reading of all twenty-five IC tags 24 and twenty-five IC tags 25 is completed is determined by the CPU 2a. If it is determined that the reading is not completed, the process returns to step S201 and the reading of a new IC tag is carried out. If it is determined that all the reading is completed, the reagent information reading process is terminated, and the process proceeds to step S3 shown in FIG. 13.

Figure 15:
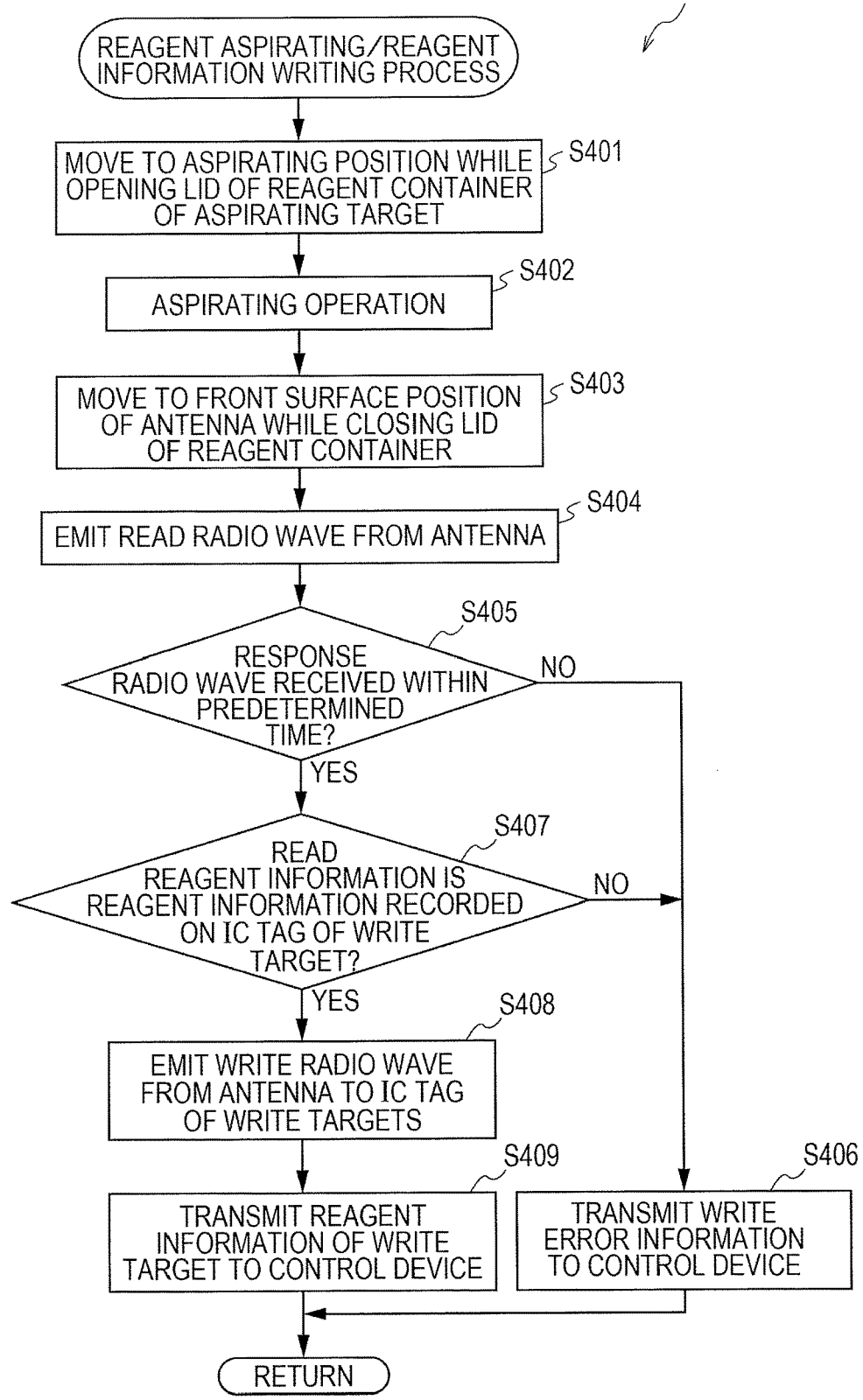
FIG. 15 is a flowchart showing a reagent aspirating/reagent information writing process of the sample analyzer F according to one embodiment shown in FIG. 1.

The reagent aspirating/reagent information writing process of the sample analyzer 1 according to the first embodiment of the present invention shown in step S4 of FIG. 13 is described in detail below with reference to FIG. 6 and FIG. 15.

First, in step S401, the R1/R3 installing portion 18 (R2 installing portion 19) is rotated in the direction of the arrow C1 (D1) or the direction of the arrow C2 (D2) (see FIG. 6) so that the reagent container to be aspirated is positioned at the reagent aspirating position. In this case, the lid of the reagent container is opened with the rotation of the R1/R3 installing portion 18 (R2 installing portion 19).

In step S402, the reagent is aspirated. Thereafter, in step S403, the R1/R3 installing portion 18 (R2 installing portion 19) is rotated in the direction of the arrow C1 (D1) or the direction of the arrow C2 (D2) so that the IC tag 24 (IC tag 25) of write target is positioned at the position facing the surface 120a on the side in the direction of the arrow X1 (surface 320a on the side in the direction of the arrow X2) of the antenna 20 by the CPU 2a. In this case, the lid of the reagent container is closed with the rotation of the R1/R3 installing portion 18 (R2 installing portion 19).

In step S404, the read radio wave is emitted from the antenna 20 to the IC tag 24 (IC tag 25) of write target by the CPU 2a. Then, in step S405, whether the antenna 20 received the response radio wave within a predetermined time is determined by the CPU 2a. If it is determined that the antenna 20 did not receive the response radio wave within a predetermined time, the reading error information is transmitted to the control device 4 and a notification that the reagent information is not written to the IC tag of the write target is displayed on the display unit 4b of the control device 4 by the CPU 2a in step S406. The reagent aspirating/reagent information writing process is then terminated, and the process proceeds to step S5 shown in FIG. 13.

If it is determined that the antenna 20 received the response radio wave within a predetermined time in step S405, whether the reagent information contained in the response radio wave received by the antenna 20 is the reagent information recorded in the IC tag of the write target is determined by the CPU 2a in step S407. In this case, the CPU 2a determines whether the reagent information recorded in the IC tag of the write target based on the reagent type (type specifying information) obtained from the response radio wave. If it is determined that the reagent information contained in the response radio wave is not the reagent information recorded in the IC tag of the write target, the process proceeds to step S406.

If it is determined that the reagent information contained in the response radio wave is the reagent information recorded in the IC tag of the write target, the write radio wave including the remaining amount information and the like of the reagent is transmitted from the antenna 20 to the IC tag 24 (IC tag 25) of the write target in step S408. In step S409, the information same as the reagent information written on the IC tag is transmitted to the control device 4, and then the reagent aspirating/reagent information writing process is terminated, and the process proceeds to step S5 shown in FIG. 13. In the control device 4, the reagent information of the storage unit 4d is updated based on the reagent information received from the CPU 2a.

In the first embodiment, the read and write of the IC tag 24 of the R1 reagent container 21 arranged in the R1/R3 installing portion 18 are carried out, and the read and write of the IC tag 25 of the R2 reagent container 23 arranged in the R2 installing portion 19 are carried out with one antenna 20. The antenna 20 thus does not need to be individually arranged with respect to each of the R1/R3 installing portion 18 and the R2 installing portion 19, and hence the number of components can be suppressed from increasing. Furthermore, only the region between the R1/R3 installing portion 18 and the R2 installing portion 19 needs to be ensured to arrange the antenna 20 by arranging the antenna 20 between the R1/R3 installing portion 18 and the R2 installing portion 19, and thus two regions do not need to be ensured to arrange the antenna 20. The main body of the sample analyzer 1 thus can be suppressed from enlarging by such an amount.

In the first embodiment, the antenna 20 is arranged so as to be sandwiched by the R1/R3 installing portion 18 formed to a substantially circular ring shape and the R2 installing portion 19 formed to a substantially circular ring shape in plan view. Thus, the R2 reagent container 23 is not positioned between the R1 reagent container 21 and the antenna 20, and the R1 reagent container 21 is not positioned between the R2 reagent container 23 and the antenna 20. Therefore, the reading of the reagent information of the IC tags 24 and 25 can be suppressed from being inhibited due to the positioning of the R2 reagent container 23 between the R1 reagent container 21 and the antenna 20 and the positioning of the R1 reagent container 21 between the R2 reagent container 23 and the antenna 20.

In the first embodiment, the IC tag 24 of the R1 reagent container 21 is attached to the side surface on the side in the direction of the arrow X2 of the reagent accommodating portion 21b of the R1 reagent container 21 so as to face (oppose) at the front surface position of the surface 120a on the side in the direction of the arrow X1 of the antenna substrate 20a, and the IC tag 25 of the R2 reagent container 23 is attached to the side surface on the side in the direction of the arrow X1 of the reagent accommodating portion 23b of the R2 reagent container 23 so as to face (oppose) at the front surface position of the surface 320a on the side in the direction of the arrow X2 of the antenna substrate 20a. Both the IC tag 24 of the R1 reagent container 21 and the IC tag 25 of the R2 reagent container 23 thus can be positioned to face the antenna 20, whereby the antenna 20 can easily read the IC tags 24 and 25.

In the first embodiment, the CPU 2a is configured to determine whether the reagent information contained in the response radio wave received by the antenna 20 is the reagent information of the read target based on the reagent type (type specifying information) contained in the response radio wave, as described above. The response radio wave from the IC tag 24 or the IC tag 25 that is not the read target is thus suppressed from being mistakenly used as the response radio wave of the read target.

Furthermore, in the first embodiment, the reader/writer substrate 17a for obtaining the reagent information from the response radio wave emitted from the IC tags 24 and 25 in response to the read radio wave and the write radio wave, and received by the antenna 20 is arranged. Thus, the reagent of the R1 reagent container 21, the reagent of the R3 reagent container 22, and the reagent of the R2 reagent container 23 can be individually managed based on the reagent information of the IC tags 24 and 25 obtained by the reader/writer substrate 17a.

Still further, in the first embodiment, the write radio wave including the reagent information to be updated is transmitted from the antenna 20 to the IC tag 24 (IC tag 25) of the write target when determined that the reagent information contained in the response radio wave is the reagent information of the read target. The CPU 2a thus can determine whether communicable with the IC tag 24 (IC tag 25) of the write target in advance before writing the reagent information to the IC tag 24 (IC tag 25) of the write target. The reagent information then can be more reliably written to the IC tag 24 (IC tag 25) of the write target.

In the first embodiment, the R1/R3 installing portion 18 is rotated in the direction of the arrow C1 or the direction of the arrow C2 by the inner side rotation drive portion 16c so that the IC tag 24 of the read target is positioned at the front surface position (opposing position) facing the surface 120a on the side in the direction of the arrow X2 of the antenna 20 when reading the reagent information of the IC tag 24 of the R1 reagent container 21, and the R2 installing portion 19 is rotated in the direction of the arrow D1 or the direction of the arrow D2 by the outer side rotation drive portion 16d so that the IC tag 25 of the read target is positioned at the position facing the surface 320a on the side in the direction of the arrow X2 of the antenna 20 when reading the reagent information of the IC tag 25 of the R2 reagent container 23. Thus, the IC tags 24 and 25 of the read target can be positioned at the position facing the surface 120a on the side in the direction of the arrow X1 and the position facing the surface 320a on the side in the direction of the arrow X2 of the antenna substrate 20a, respectively, whereby the antenna 20 can easily read the IC tags 24 and 25 of the read target.

In the first embodiment, the twenty-five R1 reagent containers 21 are arranged at equal angle (about 14.4 degrees) in the substantially circular ring shaped R1/R3 installing portion 18, and the twenty-five R2 reagent containers 23 are arranged at equal angle (about 14.4 degrees) in the substantially circular ring shaped R2 installing portion 19 arranged on the outer peripheral side of the R1/R3 installing portion 18. The metal plate 20c is arranged only on the side in the direction of the arrow X1 of the antenna 20, and the metal plate is not arranged on the side in the direction of the arrow X2 of the antenna 20. Thus, the length of the outer periphery of the R1/R3 installing portion 18 formed to a substantially circular ring shape on the inner peripheral side of the R2 installing portion 19 is smaller than the length of the inner periphery of the R2 installing portion 19, and thus the reading range of the antenna 20 can be limited to the range where only the IC tag 24 of the read target is positioned when reading the IC tag 24 proximate to each other by arranging the metal plate 20c on the side in the direction of the arrow X1 of the antenna 20 when the plurality of R1 reagent containers 21 are arranged proximate to each other than the plurality of R2 reagent containers 23, whereby the IC tag 24 that is not the read target can be easily suppressed from being mistakenly read by the antenna 20. On the R2 installing portion 19 side where the space between the adjacent R2 reagent containers 23 is wide, the readable range of the antenna 20 can be easily made large by not arranging the metal plate on the side on the direction of the arrow X2 of the antenna 20, and thus the reading of the reagent information from the IC tag 25 attached to the R2 reagent container 23 can be suppressed from failing.

The first embodiment disclosed herein is merely illustrative in all aspects and should not be recognized as being restrictive. The scope of the invention is defined by the appended claims rather than by the description of the embodiments, and all changes that fall within meets and bounds of the claims, or equivalence of such meets and bounds are therefore intended to be embraced by the claims.

For instance, an example of applying the sample analyzer of the present invention to an immune sample analyzer 1 has been described in the above first embodiment, but the present invention is not limited thereto. The present invention can be applied to any apparatus including the antenna used to read the reagent information of the electronic tag, and is also applicable to a blood coagulation analyzer, a urine specimen measurement device, a gene amplification detection device and the like other than the immune sample analyzer.

An example in which the R1/R3 installing portion 18 and the R2 installing portion 19 are arranged in a substantially circular ring shape has been described in the above embodiment, but the present invention is not limited thereto. The R1/R3 installing portion and the R2 installing portion may be arranged to extend linearly in a predetermined direction while being lined in parallel.

Figure 16:
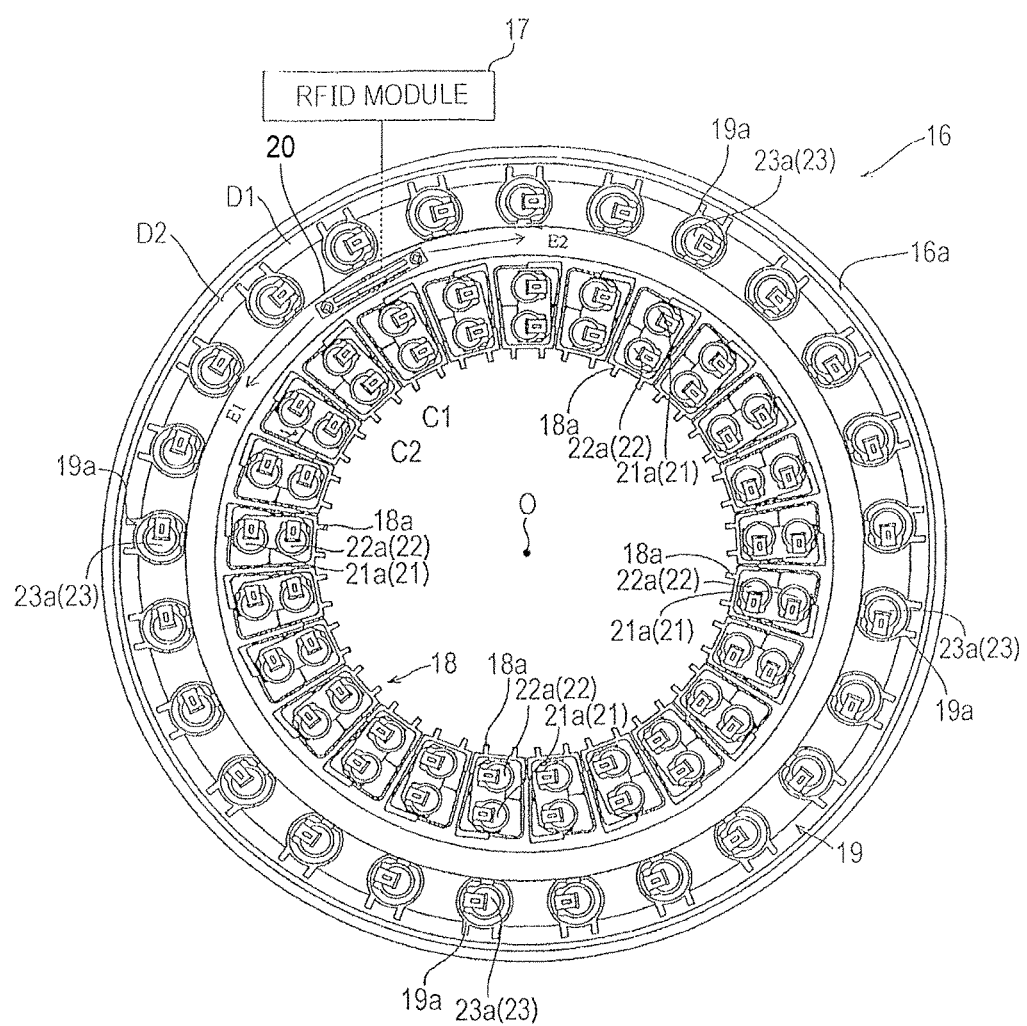
FIG. 16 is a plan view showing the interior of the reagent installing unit of the sample analyzer according to one embodiment shown in FIG. 1.

An example in which the R1/R3 installing portion 18 and the R2 installing portion 19 are rotated by the inner side rotation drive portion 16c and the outer side rotation drive portion 16d, respectively, has been described in the above first embodiment, but the present invention is not limited thereto. In the present invention, as shown in FIG. 16, the R1/R3 installing portion 18 and the R2 installing portion 19 may be configured so as not to rotate, and the antenna 20 may be configured to rotate in the direction of the arrow E1 and the direction of the arrow E2 with the center O as the center of rotation by arranging a drive portion for rotating the antenna 20.

An example in which the antenna substrate 20a can emit the read radio wave and the write radio wave has been described in the above first embodiment, but the present invention is not limited thereto. In the present invention, the antenna may be configured to emit only the read radio wave.

An example in which the metal plate 20c is arranged on the side in the direction of the arrow X1 of the antenna 20 has been described in the above first embodiment, but the present invention is not limited thereto. In the present invention, the metal plate may be arranged on the side in the direction of the arrow X2 of the antenna. Also, the metal plate may not be arranged at the antenna.

An example in which the control regarding the position of the IC tag 25 (IC tag 24) that is not the read target is not performed when the IC tag 24 (IC tag 25) of the read target is positioned at a position facing the surface 120a on the side in the direction of the arrow X1 (surface 320a on the side in the direction of the arrow X2) of the antenna 20 has been described, but the present invention is not limited thereto. In the present invention, the R2 reagent container (R1 reagent container) that is not the read target maybe moved when the IC tag of the R1 reagent container (R2 reagent container) of the read target is positioned at the position facing the surface of the antenna to move to the position where the IC tag of the R2 reagent container (R1 reagent container) that is not the read target is not read. Thus, only the IC tag of the read target can be reliably read. The IC tag of the R1 reagent container of the read target and the IC tag of the R2 reagent container of the read target may be simultaneously read in parallel with the IC tag of the R1 reagent container of the read target and the IC tag of the R2 reagent container of the read target positioned at the position facing one surface and the other surface of the antenna, respectively. A plurality of IC tags thus can be read in a short period of time.

In the above described first embodiment, the IC tag 24 is attached to the side surface on the side in the direction of the arrow X2 of the reagent accommodating portion 21b of the R1 reagent container 21 so as to face at the front surface position of the surface 120a on the side in the direction of the arrow X1 of the antenna substrate 20a. An example in which the IC tag 25 is attached to the side surface on the side in the direction of the arrow X1 of the reagent accommodating portion 23b of the R2 reagent container 23 so as to face the front surface position of the surface 320a on the side in the direction of the arrow X2 of the antenna substrate 20a has been described, but the present invention is not limited thereto. In the present invention, the IC tag may be attached to the side surface that does not face the antenna of the reagent accommodating portion as long as the IC tag can be read by the antenna.

An example in which the writing process to the IC tags 24 and 25 is performed after the reagent aspirating operation has been described in the above first embodiment, but the present invention is not limited thereto. The writing process to the IC tags may be performed before the reagent aspirating operation in the present invention.

An example in which twenty-five R1 reagent containers 21, twenty-five R3 reagent containers 22, and twenty-five R2 reagent containers 23 are arranged has been described in the first embodiment, but the present invention is not limited thereto. In the present invention, the number of the R1 reagent container, the R3 reagent container, and the R2 reagent container may differ. The number of R1 reagent container (R3 reagent container, R2 reagent container) may be other than twenty-five. For instance, only one of each of the R1 reagent container, the R3 reagent container, and the R2 reagent container may be arranged.

An example in which the metal plate 20c is arranged only on the side in the direction of the arrow X1 of the antenna 20 and the metal plate is not arranged on the side in the direction of the arrow X2 of the antenna 20 to differ the reading range by the antenna when reading the reagent information from the IC tag of the R1 reagent container and when reading the reagent information from the IC tag of the R2 reagent container, has been described in the above first embodiment, but the present invention is not limited thereto. For instance, the metal plate may be arranged on both the side in the direction of the arrow X1 and the side in the direction of the arrow X2 of the antenna, and the width of the cutout of the metal plate on the side in the direction of the arrow X1 may be formed smaller than the width of the cutout of the metal plate on the side in the direction of the arrow X2 to differ the reading range by the antenna. The CPU 2a may control the antenna substrate 20a through the reader/writer substrate 17a to emit a radio wave (radio wave of first reaching range) of large reading range (reaching range) when reading the reagent information from the IC tag 25 of the R2 reagent container 23, and the CPU 2a may control the antenna substrate 20a through the reader/writer substrate 17a to emit a radio wave (radio wave of second reaching range smaller than the first reaching range) of small reading range (reaching range) when reading the reagent information from the IC tag 24 of the R1 reagent container 21. With such a configuration, the readable range when reading the IC tag 24 can be easily made smaller than the readable range when reading the IC tag 25 by the CPU 2a.

What is claimed is:

1. A sample analyzer that analyzes a sample by using a reagent contained in a reagent container, the sample analyzer comprising:
 a first reagent container holder having a substantially circular shape and being arranged rotatably around a center point in a plan view and configured to hold at least two first-type reagent containers each containing a first-type reagent, wherein the first reagent container holder comprises a first rotation drive portion that is individually controlled to drive the first reagent container holder, wherein each of the at least two first-type reagent containers has on an outer side surface thereof, a first electronic tag carrying reagent information including type information recorded on the first electronic tags for identifying that the reagent information is of the first-type reagent, and wherein the first reagent container holder is configured to hold the first-type reagent containers in an alignment in which the first electronic tags are oriented outward with respect to the center point;

a second reagent container holder having a substantially circular shape and being rotatably arranged on an outer circumference of the first reagent container holder around the center point and configured to hold at least two second-type reagent containers each containing a second-type reagent, wherein the second reagent container holder comprises a second rotation drive portion that is individually controlled to drive the second reagent container holder, wherein each of the at least two second-type reagent containers has on an outer side surface thereof, a second electronic tag carrying reagent information including type information recorded on the second electronic tags for identifying that the reagent information is of the second-type reagent, and wherein the second reagent container holder is configured to hold the second-type reagent containers in an alignment in which the second electronic tags are oriented inward with respect to the center point;

an antenna arranged in a space between the first reagent container holder and the second reagent container holder in the plan view, the antenna comprising a first surface and a second surface on an opposite side of the first surface and being configured to emit a reading radio wave from both of the first surface and the second surface of the antenna and to receive a response radio wave generated from any of the first and second electronic tags in response to the reading radio wave;

an RFID module which retrieves the reagent information from the response radio wave received via the antenna;

a detector which measures a component contained in a measurement sample prepared by the sample and at least one of the first-type reagent and the second-type reagent; and a controller configured to:
control the first rotation drive portion to rotate and bring the first electronic tag of one of the at least two first-type reagent containers to a position in front of the first surface of the antenna when the one of the at least two first-type reagent containers is a target of reading a reagent information, control the second rotation drive portion to rotate and bring the second electronic tag of one of the at least two second-type reagent containers to a position in front of the second surface of the antenna when the one of the at least two second-type reagent containers is a target of reading a reagent information, cause the antenna to emit the reading radio wave and to receive the response radio wave including the reagent information generated in response to the reading radio wave by one of the first or second electronic tag associated with the one of the two first-type reagent containers or the one of the second-type reagent containers of the target of reading the reagent information positioned in front of the antenna, and store the reagent information retrieved from the response radio wave by the RFID module into a memory when the reagent type identified by the type information of the retrieved reagent information is equal to type information of the target of the reading the reagent information stored by the controller.

2. The sample analyzer according to claim 1, wherein the antenna is configured to emit a write radio wave to rewrite a reagent information recoded on one of the first and second electronic tags.

3. The sample analyzer according to claim 1, wherein the antenna is configured to read the second electronic tag by emitting a radio wave having a reaching range which is smaller than a reaching range of a radio wave emitted by the antenna when reading the first electronic tag.

4. The sample analyzer according to claim 3, further comprising a limiting member, which is arranged between the second electronic tag and the antenna, and is configured to limit the reaching range of the radio wave emitted by the antenna.

5. The sample analyzer according to claim 4, wherein the limiting member includes a metal member, and
a gap is formed in the metal member which is configured to pass the radio wave emitted by the antenna.

6. The sample analyzer according to claim 4, wherein the limiting member is not arranged between the first electronic tag and the antenna.

7. The sample analyzer according to claim 3, wherein the first reagent container holder is configured to hold a predetermined number of first reagent containers at equal intervals; and
the second reagent container holder is configured to hold a predetermined number of second reagent containers at equal intervals.

8. The sample analyzer according to claim 1, wherein the antenna is sandwiched between the first electronic tag and the second electronic tag such that:
an inhibition of the reading of the reagent information of the second electronic tag based on a positioning of the first electronic tag on the first reagent container between the antenna and the second electronic tag on the second reagent container in the space between the outer side surface of the first reagent container and the inner side surface of the second reagent container is suppressed, or
an inhibition of the reading of the reagent information of the first electronic tag based on a positioning of the second electronic tag on the second reagent container between the antenna and the first electronic tag on the first reagent container in the space between the outer side surface of the first reagent container and the inner side surface of the second reagent container is suppressed.

9. The sample analyzer according to claim 1, wherein the controller is configured to:
control the first rotation drive portion to rotate and bring the first electronic tag of either one of the first type of reagent container to a position in front of the first surface of the antenna;
cause the antenna to emit a reading radio wave and to receive a response radio wave generated in response to the reading radio wave by the first or second electronic tag positioned in front of the antenna, and cause the antenna to emit a write radio wave which replaces the reagent information recorded in the first or second electronic tag when the reagent type identified by the type information that is retrieved by the RFID module is equal to the reagent type of the target stored by the controller.

10. The sample analyzer according to claim 1, wherein the antenna is configured to emit the reading radio wave in a range reachable to first and second electronic tags which are placed in front of the antenna.

11. A method for obtaining reagent information of a reagent in a reagent container, the method comprising:
arranging, on a first reagent container holder comprising a substantially circular shape arranged rotatably around a center point in a plan view, at least two first-type reagent containers each containing a first-type reagent,
wherein each of the first-type reagent containers has on an outer side surface a first electronic tag carrying a reagent information including type information recorded on the first electronic tags for identifying that the reagent information is of the first-type reagent, and
wherein the first reagent container holder is configured to hold the first-type reagent containers in an alignment in which the first electronic tags are oriented outward with respect to the center point;
arranging, on a second reagent container holder comprising a substantially circular shape arranged rotatably on an outer circumference of the first reagent container holder around the center point,
wherein each of the second-type reagent containers has on an outer side surface a second electronic tag carrying a reagent information including a type information recorded on the second electronic tags for identifying that the reagent information is of second-type of reagent, and
wherein the second reagent container holder is configured to hold the second-type reagent containers in an alignment in which the second electronic tags are oriented inward with respect to the center point;
rotating the first reagent container holder to bring one of the first electronic tags to a position in front of a first surface of an antenna when the first electronic tag is a target of reading a reagent information, the antenna being arranged in a space between the first reagent container holder and the second reagent container holder in the plan view;
rotating the second reagent container holder to bring one of the second electronic tags to a position in front of a second surface of the antenna when the second electronic tag attached to the inner side surface of the second reagent container is a target of reading a reagent information; and
emitting a reading radio wave via the antenna;
receiving, via the antenna, a response radio wave including the reagent information generated in response to the reading radio wave by one of the first or second electronic tag associated with the one of the two first-type reagent containers or the one of the second-type reagent containers of the target of reading the reagent information positioned in front of the antenna, and
storing the reagent information retrieved from the response radio wave by the RFID module into a memory when the reagent type identified by the type information of the retrieved reagent information is equal to type information of the target of the reading the reagent information stored by a controller.

12. The method according to claim 11, wherein the antenna comprises a limiting member to limit a range in which the reading radio wave from the second surface reaches.

13. The method according to claim 11, wherein the antenna is sandwiched between the first electronic tag and the second electronic tag such that:
an inhibition of the reading of the reagent information of the second electronic tag based on a positioning of the first electronic tag on the first reagent container between the antenna and the second electronic tag on the second reagent container in the space between the outer side surface of the first reagent container and the inner side surface of the second reagent container is suppressed, or
an inhibition of the reading of the reagent information of the first electronic tag based on a positioning of the second electronic tag on the second reagent container between the antenna and the first electronic tag on the first reagent container in the space between the outer side surface of the first reagent container and the inner side surface of the second reagent container is suppressed.

14. A sample analyzer that analyzes a sample by using a reagent contained in a reagent container, the sample analyzer comprising:
first and second reagent container holders having circular shapes and being arranged concentrically and individually-rotatably to define: an inside track on which a plurality of first-type reagent containers loaded on the first reagent container holder run in conjunction with a rotation of the first reagent container holder; and an outside track on which a plurality of second-type reagent containers loaded on the second reagent container holder run in conjunction with a rotation of the second reagent container holder,
wherein the first reagent container holder is configured to hold the plurality of first-type reagent containers to position first electronic tags attached on a side surface of the plurality of first-type containers, which are respectively oriented outward with respect to a center point of the concentric circular shapes of the first and second reagent container holders;
wherein the second reagent container holder is configured to hold the plurality of second-type reagent containers to position second electronic tags attached on the side surface of the second-type containers, which are respectively oriented inward with respect to the center point; and
wherein each of the first and second electronic tags stores a reagent information including at least a type information for recognizing a type of reagent;
an antenna arranged in the space between the first and second reagent container holders in a plan view, wherein the antenna comprises a first surface facing to the inside track and a second surface facing to the outside track, and is configured to emit and receive radio wave via both of the first and second surfaces;
an RFID module electrically connected to the antenna;
a detector which measures a component contained in a measurement sample prepared by the sample and at least one of the first type of reagent and the second type of reagent; and
a controller configured to:

determine a target one among the plurality of first-type reagent containers and the plurality of second-type reagent containers;

drive either one of the first and second reagent container holders individually to rotate until the target one is positioned in front of the antenna;

cause the antenna to emit a reading radio wave and to receive a response radio wave generated in response to the reading radio wave by the first or second electronic tag positioned in front of the antenna, cause the RFID module to retrieve a reagent information from the response radio wave;

compare the type information in the retrieved reagent information with type information of the target stored by the controller; and store the reagent information into a memory when the controller recognizes based on comparing the type information with the type information of the target stored by the controller that the reagent information is read from the electronic tag of the target.

* * * * *